US008387530B2

(12) United States Patent
Larson et al.

(10) Patent No.: US 8,387,530 B2
(45) Date of Patent: Mar. 5, 2013

(54) PROCESS FOR MAKING A NON-WOVEN SUBSTRATE WITH VIBRANT GRAPHIC THEREON

(75) Inventors: Todd C. Larson, Grayslake, IL (US); Mark M. Mleziva, Appleton, WI (US); Brett Hoehn, Rockvale, TN (US); Walter Marsile, Murfreesboro, TN (US); Dan Conrad, Murfreesboro, TN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2989 days.

(21) Appl. No.: 10/955,803

(22) Filed: Sep. 30, 2004

(65) Prior Publication Data

US 2006/0092431 A1 May 4, 2006

Related U.S. Application Data

(60) Provisional application No. 60/584,770, filed on Jun. 30, 2004.

(51) Int. Cl.
*B41M 1/04* (2006.01)
(52) U.S. Cl. ........................................ 101/491; 101/211
(58) Field of Classification Search .................. None
See application file for complete search history.

(56) References Cited

U.S. PATENT DOCUMENTS

| | | |
|---|---|---|
| 4,105,806 A | 8/1978 | Watt |
| 4,113,895 A | 9/1978 | Watt et al. |
| 4,309,179 A | 1/1982 | Heuser et al. |
| 4,663,220 A | 5/1987 | Wisneski et al. |
| 4,706,116 A | 11/1987 | Midland et al. |
| 4,896,600 A | 1/1990 | Rogge et al. |
| 4,940,464 A | 7/1990 | Van Gompel et al. |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman et al. |
| 5,458,590 A | 10/1995 | Schleinz et al. |
| 5,562,037 A | 10/1996 | Schleinz et al. |

(Continued)

FOREIGN PATENT DOCUMENTS

| | | |
|---|---|---|
| CN | 1340650 | 3/2002 |
| EP | 0 217 032 A2 | 4/1987 |

(Continued)

OTHER PUBLICATIONS

International Search Report for PCT/US2005/014960, dated Aug. 23, 2005, 3 pages.

(Continued)

*Primary Examiner* — Joshua D Zimmerman
(74) *Attorney, Agent, or Firm* — Armstrong Teasdale LLP

(57) ABSTRACT

A non-woven substrate having a vibrant graphic applied thereto is made by feeding to a printing apparatus a non-woven substrate having a fibrous non-woven web formed at least in part of polyolefin fibers. An ink composition having a viscosity in the range of about 28 seconds to about 35 seconds as determined using a Zahn #2 cup and including at least one solvent having an evaporation rate relative to n-butyl acetate of less than 0.8 is supplied to the printing apparatus. The printing apparatus is operated to apply the ink composition to the fibrous non-woven web while the fibrous non-woven web is in a generally dry condition to form a graphic thereon having a thickness of less than or equal to about 5 microns. The ink composition is then allowed to dry on the fibrous non-woven web.

24 Claims, 6 Drawing Sheets

U.S. PATENT DOCUMENTS

| | | | |
|---|---|---|---|
| 5,566,616 A | 10/1996 | Schleinz et al. | |
| 5,593,940 A | 1/1997 | Umise et al. | |
| 5,766,389 A | 6/1998 | Brandon et al. | |
| 5,837,352 A | 11/1998 | English et al. | |
| 5,843,056 A | 12/1998 | Good et al. | |
| 6,075,179 A | 6/2000 | McCormack et al. | |
| 6,096,412 A | 8/2000 | McFarland et al. | |
| 6,309,736 B1 | 10/2001 | McCormack et al. | |
| 6,477,948 B1 | 11/2002 | Nissing et al. | |
| 6,645,190 B1 | 11/2003 | Olson et al. | |
| 6,649,808 B1 | 11/2003 | Tao et al. | |
| 6,653,523 B1 | 11/2003 | McCormack et al. | |
| 2002/0025752 A1 | 2/2002 | Taniguchi | |
| 2003/0019374 A1 | 1/2003 | Harte | |
| 2003/0144375 A1* | 7/2003 | Wu et al. | 523/160 |
| 2003/0154871 A1 | 8/2003 | Laksin et al. | |
| 2004/0121675 A1 | 6/2004 | Snowden et al. | |
| 2004/0265516 A1 | 12/2004 | Schulz et al. | |
| 2005/0191439 A1* | 9/2005 | Hirose et al. | 428/32.1 |

FOREIGN PATENT DOCUMENTS

| | | |
|---|---|---|
| WO | WO 95/15410 A1 | 6/1995 |
| WO | WO 96/16809 A1 | 6/1996 |
| WO | WO 00/37009 A2 | 6/2000 |
| WO | 0053429 A1 | 9/2000 |
| WO | WO 00/60916 A2 | 10/2000 |
| WO | WO 01/88245 A2 | 11/2001 |
| WO | 0196122 A1 | 12/2001 |
| WO | WO 2005/014297 A1 | 2/2005 |

OTHER PUBLICATIONS

International Search Report for PCT/US2005/014944, dated Aug. 19, 2005, 3 pages.

Communication from the Examining Division received in EP Patent Application No. 05743639.6, mailed Oct. 7, 2011.

* cited by examiner

PROCESS FOR MAKING A NON-WOVEN SUBSTRATE WITH VIBRANT GRAPHIC THEREON

REFERENCE TO RELATED APPLICATIONS

This application claims priority from provisional application Ser. No. 60/584,770 filed Jun. 30, 2004 and entitled Non-Woven Substrate With Vibrant Graphic Thereon and Method of Making Same.

BACKGROUND OF THE INVENTION

This invention relates generally to substrates used in making articles such as training pants, diapers, feminine hygiene products, incontinence garments and the like, and more particularly to such substrates having graphics thereon.

Personal wear articles find widespread use as personal care products including, without limitation, diapers, children's toilet training pants, adult incontinence garments, sanitary napkins and the like, as well as surgical bandages and sponges. Certain such articles are generally considered to be disposable in that they are usually intended to be discarded after a limited period of use, i.e., the articles are not intended to be laundered or otherwise restored for reuse. Disposable absorbent articles typically comprise an absorbent body disposed between a liner, which contacts the wearer's skin, and an outer cover, which inhibits liquid body waste absorbed by the absorbent body from leaking out of the article. The liner of the absorbent article is typically liquid permeable to permit liquid body waste to pass therethrough for absorption by the absorbent body.

Conventional absorbent articles also typically include some type of fastening system for securing the absorbent article in an assembled configuration and/or for fitting the article on the wearer, such as on the wearer's waist in the case of diapers and training pants. In many such applications, the fastening system is releasable and refastenable so that the article can be temporarily removed and then refastened to the wearer.

It is further known to apply a graphic, such as in the form of a character, fabric pattern, undergarment markings, object and/or alphanumeric (e.g., numbers, words, phrases, instructions, etc.) to personal wear articles to enhance the aesthetic or otherwise visual appearance or usefulness of the article. Graphics applied to such articles may also provide visual assistance to the wearer or to a caregiver securing the article on the wearer. In some instances, the graphics may include a material or substance capable of being visible in low light conditions, including in the dark, to further enhance the appeal to the wearer or ease of use by the caregiver.

One common technique used to apply a graphic to a personal wear article, and more particularly to the outer cover thereof, is commonly known as flexographic printing and provides a cost effective, high speed, high quality printing technique for printing thin films or non-woven fibrous webs while maintaining the tactile softness of the film or web. Flexography involves the use of flexible, raised rubber or photopolymer print plates to carry an image to a given substrate onto which the graphic is transferred. More specifically, an anilox roll is rotated through an ink reservoir to become coated with ink and then further rotated into contact with a print cylinder on which the print plate is mounted. The ink is transferred from the anilox roll onto the print plate. The print cylinder rotates relative to an impression cylinder over which the substrate moves whereby the ink covered print plate presses against the substrate (and impression cylinder) to transfer the ink from the print plate to the substrate to create the desired graphic.

It is becoming more desirable that absorbent articles appear more like conventional garments. For example, children's toilet training pants desirably appear more similar to conventional children's cloth underpants. One feature that would facilitate such an improved appearance is brighter, more vibrant graphics on absorbent articles. Compared to graphics on printed cloth underpants, flexographic printed non-woven substrates incorporated into training pants yield a visually dull graphic. It is also common to print graphics on a film layer that is then overlaid by a non-woven layer (e.g., to provide a softer, more cloth-like feel and appearance). However, covering the film layer also tends to dull the graphics imprinted on the film layer.

One readily apparent approach to improve the vibrancy of the graphics applied by flexographic printing to non-woven webs would be to increase 1) the volume of ink held by the anilox roll and 2) to increase the impression pressure of the print cylinder (i.e., the pressure applied by the print cylinder against the impression cylinder). That is, by increasing the ink volume and pressing the print plate harder against the substrate, it is expected that the vibrancy of the graphic would increase. While such process changes can improve printed graphic vibrancy, increased impression pressure, by itself, does not yield a significant improvement in vibrancy. Moreover, too much impression pressure can distort the graphic. Increasing the ink volume on the anilox roll also does not yield significant improvement of the graphic vibrancy. Specifically, solely increasing the volume of ink on the anilox roll does not translate into a greater volume of ink transferred to the non-woven substrate to increase the vibrancy of the graphic.

It is also known that printing vibrant images on polyolefin fibrous non-woven webs, and in particular those made from polypropylene fibers, is difficult.

There is a need, therefore, for high vibrancy graphics applied to non-woven substrates (e.g., having irregular surfaces), particularly by flexographic printing. More particularly, it is desirable that such high vibrancy graphics be achieved with a relatively thin layer of ink applied to the non-woven substrate to thereby maintain the soft, clothlike texture of the non-woven substrate. There is also a need to improve the vibrancy of graphics on absorbent articles while maintaining or improving the cost efficiency associated with the manufacture of such articles.

SUMMARY OF THE INVENTION

In general a process according to one embodiment of the present invention for making a non-woven substrate having a vibrant graphic applied thereto comprises feeding to a printing apparatus a non-woven substrate comprising a fibrous non-woven web composed at least in part of polyolefin fibers. An ink composition having a viscosity in the range of about 28 seconds to about 35 seconds as determined using a Zahn #2 cup and comprising at least one solvent having an evaporation rate relative to n-butyl acetate of less than 0.8 is supplied to the printing apparatus. The printing apparatus is operated to apply the ink composition to the fibrous non-woven web while the fibrous non-woven web is in a generally dry condition to form a graphic thereon having a thickness of less than or equal to about 5 microns. The ink composition is then allowed to dry on the fibrous non-woven web.

Other features of the invention will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
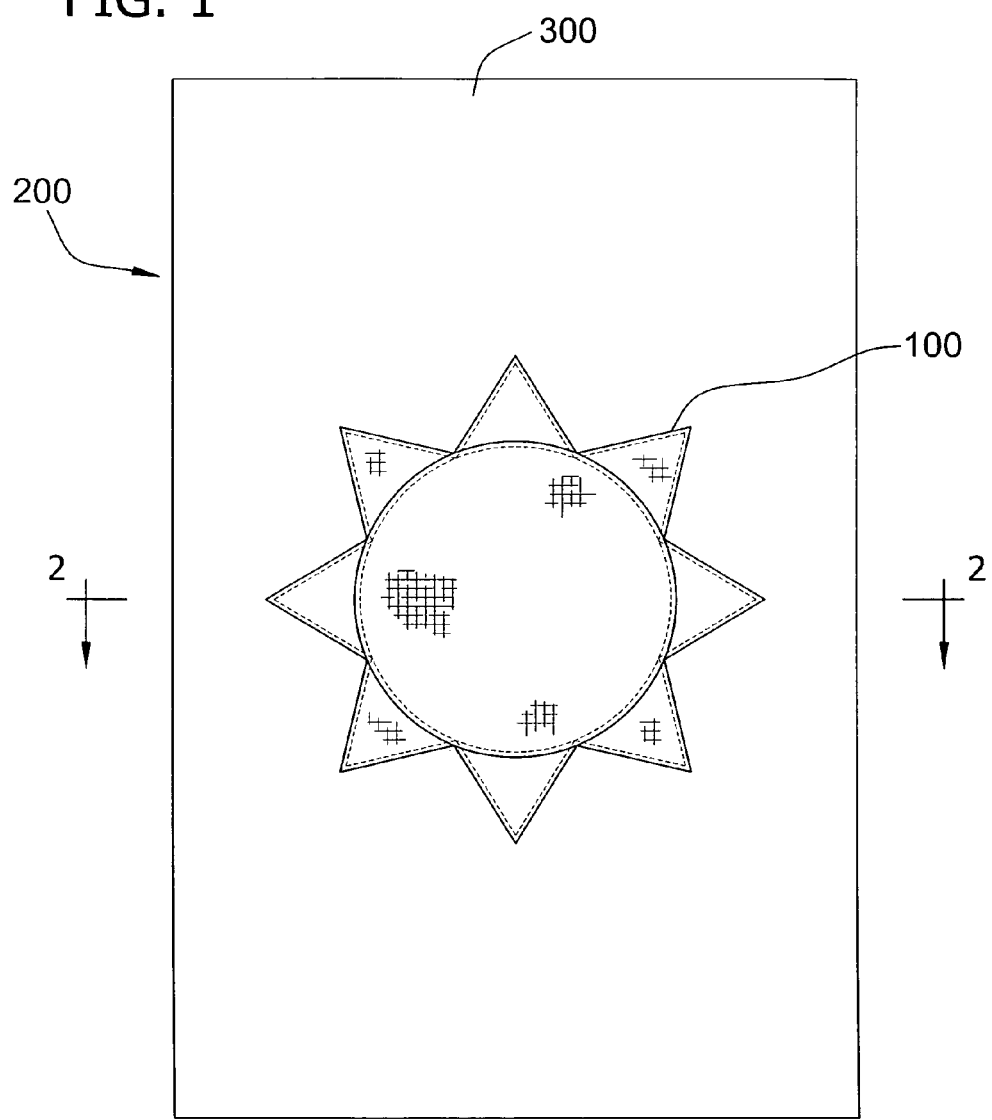
FIG. 1 is a top plan view of a non-woven substrate of the present invention having a graphic applied thereto.
Figure 2:
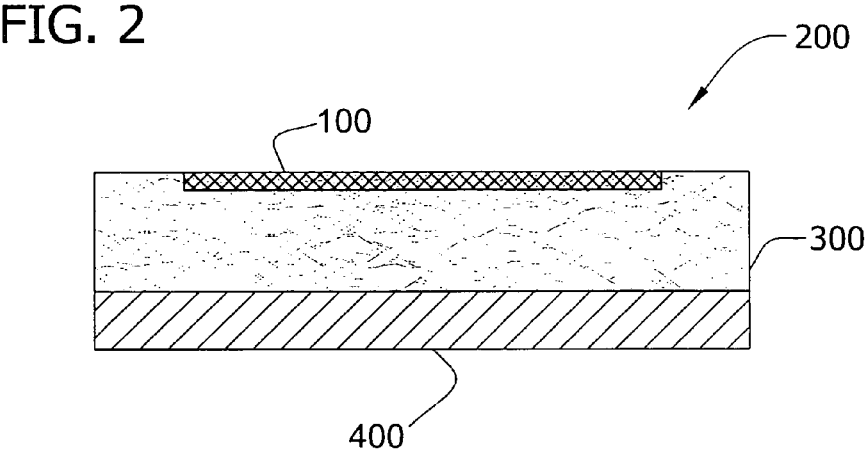
FIG. 2 is a cross-section of the non-woven substrate taken in the plane of line 2-2 of FIG. 1.

Referring now to the drawings and in particular to FIG. 1, the present invention is generally directed to the application of one or more graphics, such as the graphic 100 depicted in the illustrated embodiment, to a non-woven substrate, generally indicated at 200. In a particularly suitable embodiment, the non-woven substrate 200 comprises a multi-layered laminate wherein at least one outer layer of the laminate is a fibrous non-woven web. For example, as shown in FIG. 2 the non-woven substrate 200 may comprise a fibrous non-woven web 300 adhesively laminated to a film layer 400. In such an embodiment wherein the non-woven substrate 200 is a multi-layered laminate, the graphic 100 is preferably applied to the fibrous non-woven web 300 of the substrate 200. It is contemplated that in other embodiments the non-woven substrate may instead comprise a single fibrous non-woven web.

The non-woven substrate 200 may optionally be stretchable, such as elastomeric or extensible. As used herein, the term "stretchable" refers to a material that may be extensible or elastomeric. That is, the material may be extended, deformed or the like, without breaking, and may or may not significantly retract after removal of an extending force. The terms "elastomeric" or "elastic" are used interchangeably herein and refer to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent elongation or the material does not exhibit a significant retractive force.

In particular, elastomeric materials utilized in connection with the non-woven substrate 200 of the present invention may be elongated/extended or stretched in at least one direction without breaking by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally preferable that the elastomeric material or composite be capable of being elongated by at least 100%, more preferably by at least 200%, of its relaxed length and recover at least 30% and more preferably 50% of its elongation upon release of a stretching, biasing force, within about one minute.

Similarly, the extensible or elongatable materials may be capable of stretching in at least one direction without breaking by at least 25% (to at least 125% of its initial unstretched length) in at least one direction, suitably by at least 50% (to at least 150% of its initial unstretched length), more suitably by at least 100% (to at least 200% of its initial unstretched length). As an example, an extensible material having an initial unstretched length of 3 inches (7.6 centimeters) may be stretched without breaking to a stretched length of at least 3.75 inches (9.5 centimeters) in at least one direction (for the "by at least 25%" value). The stretchable material may be stretchable in multiple directions, e.g., both the lateral and longitudinal directions, or it may be stretchable in only one of the lateral and longitudinal directions.

Suitable elastomeric structures for use in connection with the non-woven substrate 200 can include elastic strands, LYCRA elastics, nonwoven elastic webs, meltblown or spunbond elastomeric fibrous webs, as well as combinations thereof, and/or laminates in which the fibrous non-woven web is laminated to an elastomeric layer. Examples of suitable elastomeric materials include multi-block elastomeric copolymers which may be obtained from Kraton Polymers under the trade designation KRATON elastomeric resin; polyurethanes, such as those available from E.I. duPont de Nemours Co. under the trade designation LYCRA polyurethane; polyamides, such as polyether block amides available from Atofina Chemical Co. of Philadelphia, Pa. under the trade designation PEBAX polyether block amide; polyesters such as those available from E.I. duPont de Nemours Co. under the trade designation HYTREL polyester; and single-site or metallocene-catalyzed polyolefins having density less than about 0.89 grams/cubic centimeter, such as that available from Dow Chemical Co. under the trade designation AFFINITY.

The fibrous non-woven web 300 of the non-woven substrate 200 may suitably comprise a meltblown web, a spun-bonded web, a spunbond-meltblown web, a spunbond-meltblown-spunbond web, a bonded-carded-web, a hydroentangled or hydroknit web, an airformed web, a needlepunched web or other non-woven web of fibers, or combinations thereof. In particularly suitable embodiments, the fibrous non-woven web 300 of the substrate 200 is comprised at least in part of polyolefin fibers. Examples of suitable polyolefins include polypropylene and polyethylene, including high density, low density and linear low density polyethylene.

The term fiber as used in reference to construction of the fibrous non-woven web 300 refers to fibers that may have the same general construction or composition throughout, and to fibers that may be multicomponent fibers in which at least one component is a polyolefin. For example, the fibrous non-woven web 300 may comprise bicomponent fibers having a sheath/core configuration in which the sheath is a polyolefin. The core may also suitably be a polyolefin. It is also contemplated that the fibers may be multicomponent fibers having other than a sheath/core configuration, such as a side-by-side configuration, islands-in-sea configuration and eccentric fiber configurations. It is also contemplated that the fibers need not be circular in cross-section. For example, the fibers may have a "Y" shaped or "X" shaped cross-section. The fibers are also suitably sized in the range of about 0.1 to about 10 denier. However, larger or smaller sized fibers may be used without departing from the scope of this invention. The polyolefin fibers may also include one or more additives, such as less than about 10 percent by weight add-on, for particular fiber property enhancements. Such additives include, without limitation, UV stabilizers, antioxidants, surfactants, process aids, molecular weight modifiers, flow modifiers, coloring pigments such as $TiO_2$, and other suitable additives.

In one embodiment, the fibrous non-woven web 300 comprises at least about 10 percent by weight polyolefin fibers (single component or multi-component), more suitably at least about 20 percent, and even more suitably up to 100 percent. The polyolefin fibers are suitably hydrophilic, e.g., having a relatively high wettability. The term hydrophilic describes fibers or the surfaces of fibers which are wetted by aqueous liquids in contact with the fibers. The degree of wetting can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

In one example of a particularly suitable embodiment, the fibrous non-woven web 300 comprises spunbond bicomponent fibers each having a sheath/core configuration wherein the core is polypropylene and the sheath is linear low density polyethylene (LLDPE). Alternatively, the core of the bicomponent fibers may be polypropylene or other suitable material. One example of a fibrous non-woven web 300 comprised of such bicomponent fibers is a 34 grams per square meter (gsm) spunbond non-woven and comprises approximately 2.5 denier bicomponent fibers having a 20 percent by weight LLDPE concentric sheath and an 80 percent by weight elastic metallocene-catalyzed polyethylene core. It is also contemplated that the sheath of the bicomponent fibers may instead be constructed of polypropylene or other suitable materials without departing from the scope of this invention. The fibrous non-woven web 300 suitably has a basis weight in the range of about 10 to about 90 gsm, and more suitably in the range of about 15-35 gsm.

In other embodiments the fibrous non-woven web 300 may be constructed at least in part of other polymer and/or copolymer fibers (e.g., other than polyolefin fibers), including without limitation random copolymers, block copolymers, alternating copolymers, graft copolymers, polymer blends, and modifications thereof.

The fibers of the fibrous non-woven web 300 are suitably bonded together, such as by ultrasonic bonding, thermal bonding, and the like. As an example, the fibrous non-woven web 300 suitably has a bond pattern comprising less than or equal to about 20 percent of the surface area of the web surface on which the graphic 100 is applied, and more suitably in the range of about 10 percent to about 20 percent thereof, so as to minimize any corruption of the visual appearance of the graphic applied to the non-woven substrate. This includes any bonding of the non-woven web 300 itself plus any subsequent bonding of the non-woven web to a backing layer (such as the film 400) when forming a laminate non-woven substrate 200.

For embodiments in which the non-woven substrate 200 comprises a laminate, the fibrous non-woven web 300 may be bonded to a foam layer, a cast film (single or multiple layer), a blown film (single or multiple layer) or other suitable backing material. The laminate substrate 200 may be stretchable or non-stretchable. In one particularly suitable embodiment, the non-woven substrate 200 is a spunbond-film laminate comprised of a spunbond fibrous non-woven web 300 bonded to a film material 400. The film or other backing layer to which the non-woven web is bonded to form a laminate non-woven substrate suitably has a basis weight in the range of about 10-35 gsm. One example of a particularly suitable film is a 19 gsm microporous, breathable, cast, white film available from Pliant Corporation as model designation XP-8600.

In another embodiment, the laminate substrate 200 may comprise an adhesive stretch film laminate in which a non-woven web adhered to a multi-layer film. The film comprises an extruded thermoplastic polymer core layer and thermoplastic polymer skin layers coextruded with the core layer on opposite sides thereof. The multi-layer film is stretched to substantially thin the skin layers, e.g., to about 2 microns or less. Suitable examples of such laminate substrates are described in U.S. Pat. No. 5,843,056 (Good et al.); U.S. Pat. No. 6,075,179 (McCormack et al.); U.S. Pat. No. 6,309,736 (McCormack et al.); and U.S. Pat. No. 6,653,523 (McCormack et al.), the entire disclosures of which are incorporated herein by reference.

The fibrous non-woven web 300 is preferably adhesively bonded to the film layer 400. The adhesive can be applied, for example, by melt spraying, printing, coating such as slot coating, or meltblowing. In one particularly suitable embodiment, the fibrous non-woven web 300 is adhesively bonded to the film layer 400 using 3 gsm of a hot melt adhesive available from Bostik-Findley of Milwaukee, Wis. as model designation H2096. It is understood, however, that other bonding techniques, such as thermal bonding, ultrasonic bonding, pressure bonding, autogenous bonding of components such as in extrusion coating, or other suitable bonding techniques may be used.

Suitable graphics 100 that may be applied to the non-woven substrate 200 include, but are not limited to, scenes, characters, fabric patterns, random patterns, garment components such as waistbands, leg bands, labels, animals, objects, alphanumerics such as numbers, letters, words, phrases and the like. The graphic 100 is formed from an ink composition comprising a resin, including, but not limited to, acrylic, urethane, polyamide, polyketone, polyvinyl butyral, shellac and nitrocellulose based resins; a colorant, such as a pigment; and a solvent or solvent blend. The ink composition may, but need not necessarily, further include a binder and/or wax, crosslinking agents, pH control agents, preservatives, viscosity modifiers, defoamers, dispersants, and corrosion control agents. The term "ink composition" as used in reference to the graphic 100 refers to the ink composition as initially applied to the substrate, it being understood that certain components of the ink composition will evaporate following application to form the graphic applied to the non-woven substrate.

Suitable pigments include azo dyes (for example, Solvent Yellow 14, Dispersed Yellow 23, and Metanil Yellow), anthraquinone dyes (for example, Solvent Red 111, Dispersed Violet 1, Solvent Blue 56, and Solvent Orange 3), xanthene dyes (Solvent Green 4, Acid Red 52, Basic Red 1, and Solvent Orange 63), azine dyes (for example, Jet Black), and the like.

Major organic pigments include dairylide yellow AAOT (for example, Pigment Yellow 14 CI#21095), dairylide yellow AAOA (for example, Pigment Yellow 12 CI#21090), Phthalocyanine Blue (for example, Pigment Blue 15), lithol red (for example Pigment Red 52:1 CI#15860:1), toluidine red (for example, Pigment Red 22 (CI#12315), dioxazine violet (for example, Pigment Violet 23 CI#51319), phthalocyanine green (for example, Pigment Green 7 CI#74260), phthalocyanine blue (for example, Pigment Blue 15

(CI#74160), napthoic acid red (for example, Pigment Red 48:2 CI#15865:2). Inorganic pigments include titanium dioxide (for example, Pigment White 6 CI#77891), carbon black (for example, Pigment Black 7 CI#77266), iron oxides (for example, red, yellow and brown), ferric oxide black (for example, Pigment Black 11 CI#77499), chromium oxide (for example, green), ferric ammonium ferrocyanide (for example, blue), and the like.

The pigment to binder ratio of the ink composition is suitably in the range of about 5 percent/95 percent (e.g., 1:19) to about 60 percent/40 percent (e.g., 1.5:1), and more suitably in the range of about 45 percent/55 percent (e.g., 1:1.2) to about 60 percent/40 percent (e.g., 1.5:1).

Suitable solvents for the ink composition include, without limitation, alcohols, acetates, ketones, glycol ethers, aromatic hydrocarbons, aliphatic naphthas, water and combinations thereof. As an example, suitable alcohols include ethyl alcohol, isopropyl alcohol, N-propyl alcohol, and blends thereof. Suitable acetates include ethyl acetate, N-propyl acetate, N-butyl acetate, isopropyl acetate, isobutyl acetate, butyl acetate, and blends thereof. Suitable glycol ethers include ethylene glycol monopropyl ether, ethylene glycol monobutyl ether, diethylene glycol monomethyl ether, diethylene glycol monopropyl ether, propylene glycol monomethyl ether, polyproylene glycol n-propyl ether, and blends thereof.

In accordance with one embodiment of the present invention, the solvent or solvent blend in the ink composition suitably includes a "slow drying" solvent. It is believed that such a solvent allows increased time for the ink composition to wick, e.g., flow, within the fibrous non-woven web and coat the fibers therein upon application of the graphic thereto before the ink composition dries. As used herein, a slow drying solvent refers to a solvent having a relatively low evaporation rate relative to n-butyl acetate. The following table identifies the evaporation rate for various solvents normalized relative to n-butyl acetate (i.e., the evaporation rate of n-butyl acetate=1.0). Thus, a number lower than 1 identifies the solvent as having an evaporation rate that is slower than that of n-butyl acetate.

|  | Evaporation Rate (n-Butyl Acetate = 1) |
| --- | --- |
| Water | 0.82 |
| Ethyl Acetate | 7.47 |
| Isopropyl Acetate | 4.55 |
| n-Propyl Acetate | 2.73 |
| Ethyl Alcohol | 3.30 |
| Isopropyl Alcohol | 2.83 |
| n-Propyl Alcohol | 1.30 |
| Ethylene Glycol | 0.0036 |
| Propolyene Glycol | 0.0053 |
| Dipropylene Glycol | 0.0008 |
| Propylene Glycol Methyl Ether | 0.71 |
| Dipropylene Glycol Methyl Ether | 0.02 |
| Propylene Glycol n-Propyl Ether | 0.21 |
| Dipropylene Glycol n-Butyl Ether | 0.01 |

More particularly, the solvent or solvent blend includes a slow drying solvent having an evaporation rate relative to n-butyl acetate of less than 0.8, more suitably less than about 0.5, and even more suitably less than about 0.25. While glycol ethers as a family are slow drying solvents, one example of a particularly suitable solvent is propylene glycol n-propyl ether (PnP), which has an evaporation rate relative to n-butyl acetate of about 0.21.

The solvent or solvent blend also suitably has a relatively low surface tension to thereby reduce the overall surface tension of the ink composition. It is desirable that the ink composition has a relatively low surface tension compared to the surface tension of the fibers of the fibrous non-woven web to facilitate enhanced wetting of the fibers by the ink composition. Enhanced fiber wicking provides desirable ink distribution about (e.g., coating of) the fibers of the fibrous non-woven web 300. As a particular example, the PnP solvent has a surface tension of about 27 dyne/cm at 25 degrees Celsius.

In one suitable embodiment, the ink composition includes a solvent blend comprising about 35 to about 50 weight percent n-propyl alcohol, zero to about 15 weight percent n-propyl acetate and about 40 to about 60 weight percent PnP. More suitably, the solvent blend comprises about 45 weight percent n-propyl alcohol, about 5 weight percent n-propyl acetate and about 50 weight percent PnP.

The amount of solvent or solvent blend used is suitably sufficient to render the viscosity of the ink composition (in print ready condition) to be in the range of about 20 to about 35 seconds as determined using a Zahn #2 cup. More suitably, in accordance with one particular embodiment of the present invention, the amount of solvent is sufficient so that the final (print ready) ink composition has a relatively high viscosity, such as in the range of about 28 to about 35 seconds as determined using a Zahn #2 cup.

As one example of a suitable ink composition for use with the present invention, an ink composition was prepared from a nitrocellulose based ink available from Sun Chemical Corporation of Fort Lee, N.J., U.S.A. under the designation PYROFLEX. The ink was further reduced by an additional 20 percent by mixing the ink with a solvent blend comprising PnP, n-propyl alcohol and n-propyl acetate. More particularly, the blended ink composition comprised about 50 weight percent of the initial ink and about 50 weight percent of the solvent blend. The final (e.g., print ready) ink composition had a viscosity in the range of about 28 to about 32 seconds using a Zahn #2 cup. The total blend of solvent in the ink composition included about 50 weight percent PnP, about 35 weight percent n-propyl alcohol and about 15 weight percent n-propyl acetate.

It is understood that the ratio of initial ink to added solvent blend can vary to achieve the desired viscosity without departing from the scope of this invention. It is also understood that other solvent blends may be used without departing from the scope of this invention, as long as the solvent blend includes a slow drying solvent to thereby decrease the evaporation rate of the final (e.g., print ready) ink composition In accordance with one embodiment of a method of the present invention for making a non-woven substrate 200 having a high vibrancy graphic 100 applied thereto, the ink composition is applied to the fibrous non-woven web 300 of the substrate while the fibrous non-woven web 300 is in a substantially dry condition, with the resultant ink film thickness of the graphic being less than or equal to about 5 microns, and more suitably less than or equal to about 2 microns. The thickness of the graphic 100 is referred to herein as meaning the thickness of the print layer, or ink film or coating, deposited on the fibrous non-woven web 300, including portions of the print layer that bridge spans between fibers and are deposited on bond points within the non-woven web. One suitable apparatus for applying the ink composition to the non-woven substrate 200 to form the relatively thin graphic 100 is a flexographic printing process. Flexographic printing is a conventional printing technique which uses flexible, raised rubber or photopolymer print plates to transfer an inked image to a substrate.

Figure 3:
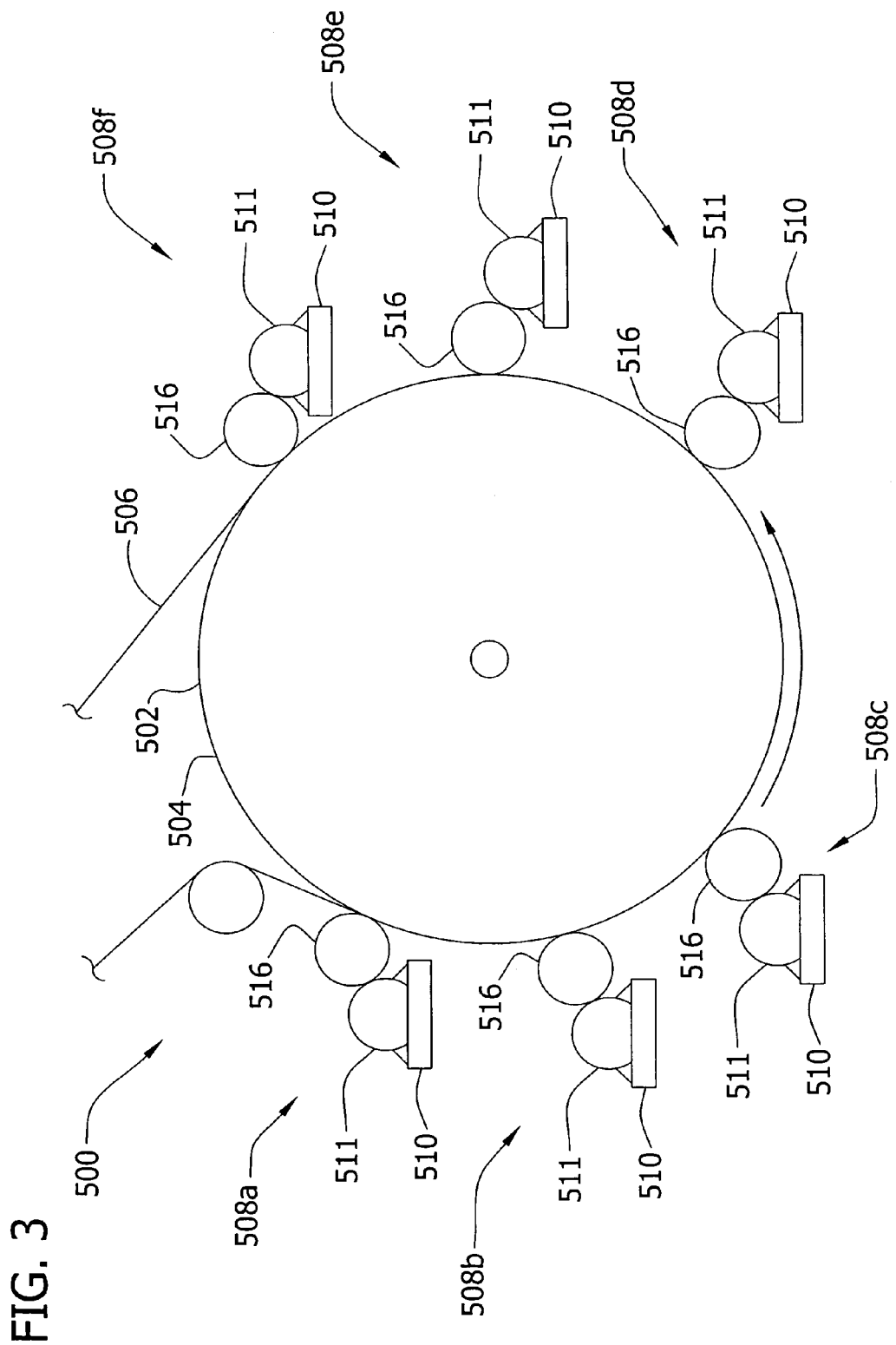
FIG. 3 is a schematic of a flexographic printing apparatus.

FIG. 3 schematically illustrates a flexographic printing apparatus, generally indicated at 500, comprising a central rotary impression cylinder 502 having a circumferential outer surface 504 on which a continuous non-woven substrate 506 (e.g., constructed in the manner of the non-woven substrate 200 of FIGS. 1 and 2) is transported by the impression cylinder in the direction of rotation thereof as indicated by the directional arrow in FIG. 3. It is generally preferred that the non-woven substrate 506 comprise a laminate such as that shown in FIGS. 1 and 2 and described previously, with the fibrous non-woven web of the substrate facing away (e.g., outward) of the impression cylinder 502 outer surface. While less preferred, it is understood that the non-woven substrate 506 may instead comprise only a fibrous non-woven web (e.g., such as the fibrous non-woven web 300 of FIGS. 1 and 2), which may or may not be subsequently laminated to another layer of material, and remain within the scope of this invention.

Print stations (six are shown in FIG. 3 and indicated generally at 508a, 508b, 508c, 508d, 508e and 508f) are positioned about the impression cylinder 502 in opposed relationship with the circumferential outer surface 504 of the impression cylinder. Each print station 508a, 508b, 508c, 508d, 508e and 508f comprises an ink composition delivery and metering chambered doctor blade 510, and anilox (or metering) roll 511 rotatable into contact with the doctor blade so that discrete cells formed in the outer surface of the anilox roll become filled with a predetermined volume of ink composition, and a print cylinder 516 carrying a raised rubber or photopolymer plate (not shown) corresponding to the desired graphic. The print cylinder 516 is rotatable to rotate the print plate into contact with the anilox roll 511 whereby ink composition from the anilox roll is transferred to the print plate. Further rotation of the print cylinder 516 rotates the inked print plate into contact with the non-woven substrate 506 so that the substrate becomes disposed within a nip formed between the print plate and the impression cylinder 502.

The print stations 508a, 508b, 508c, 508d, 508e, 508f are each moveable relative to the impression cylinder 502 to allow adjustment of the pressure-applied by the print plate against the impression cylinder (and hence the non-woven substrate 506). The impression pressure can effect the amount of ink composition that is transferred from the print plate onto the fibrous non-woven web of the substrate 506. For example, where the impression pressure is too low, an insufficient amount of ink will be transferred to the fibrous non-woven web and the resultant graphic will be faint, or dull, whereas too high of an impression pressure can result in too much ink transferred to the fibrous non-woven web such that the graphic appears smeared. As used herein, the impression pressure of the print plate against the impression cylinder 502 is defined as the set point of the print plate relative to a zero position set point in which the print plate touches the impression cylinder with zero pressure therebetween. A positive set point means movement of the print plate further inward against the impression cylinder 502 so as to apply a pressure thereto. As an example, the set point of the print plate in accordance with one embodiment of the present invention is suitably in the range of about 0.115 to about 0.135 inches.

The print stations 508a, 508b, 508c, 508d, 508e and 508f may contain ink compositions of different colors or ink types to be used in forming an entire graphic, or multiple graphics on the non-woven substrate 506. Less than all of the print stations may be used, including the use of a single print station where a unitary color graphic is to be applied to the non-woven substrate 506.

Particular construction and operation of the flexographic printing apparatus 500 is well known to those skilled in the art and will not be further described herein except to the extent necessary to describe the present invention. As an example, flexographic printing apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.). In one particularly suitable embodiment, the flexographic printing apparatus is configured for block printing, wherein the printing plate contains solid regions that are raised and are in the shape of the desired graphic so that a continuous or solid graphic is applied to the non-woven substrate. In another suitable embodiment, the printing plate is configured for line printing, which is known to those skilled in the art. However, it is contemplated that the flexographic printing apparatus may be instead be configured for dot process printing or stochastic printing, both of which are also well-known to those skilled in the art. Certain ink compositions may be applied over previously applied compositions as the substrate 506 is fed through the printing apparatus to thereby create the desired color of the graphic.

It is understood that conventional printing techniques other than flexographic printing may used to apply the graphic to the non-woven substrate without departing from the scope of this invention. For example, other suitable printing techniques include, without limitation, screen printing, rotogravure printing in which an engraved print roll is utilized, and ink jet printing.

In accordance with one embodiment of the present invention, at least one of the ink composition, the non-woven substrate 506 and the printing apparatus 500 used to apply the ink composition to the non-woven substrate are configured such that the resultant graphic applied to the non-woven substrate has a relatively high vibrancy. The vibrancy of the graphic as used herein refers to the color density of the graphic, i.e., the density of the color produced by the ink composition on the non-woven substrate. The human eye assessment of the strength of a color is not related to the reflectance in a linear manner, but is rather more nearly a logarithmic relationship. More specifically, color density is empirically defined by the equation:

$$\text{Density} = \log_{10}(I/R)$$

where;

I is the intensity of incident light and

R is the intensity of reflected light.

A higher color density equates to a higher vibrancy or intensity of the color. In particular, as used herein, the color density of the graphic refers to the color density of the dominant primary color of a graphic (e.g., yellow, magenta, cyan or black) as determined using a densitometer in accordance with the Color Density Test set forth below. Suitably, the color density of the dominant primary color of the graphic of the present invention is at least about 0.5. In other embodiments, the color density of the dominant primary color of the graphic is suitably at least about 0.7. And in other embodiments the color density of the dominant primary color of the graphic is suitably at least about 0.8.

More particularly, where the dominant primary color of the graphic is magenta, the color density of the dominant primary color is at least about 0.5, more suitably at least about 0.6, even more suitably at least about 0.7, and still more suitably at least about 0.8. Where the dominant primary color of the graphic is black, the color density of the dominant primary color is at least about 0.5, more suitably at least about 0.6, even more suitably at least about 0.7, and still more suitably at least about 0.8. Where the dominant primary color of the graphic is cyan, the color density of the dominant primary color is at least about 0.5, more suitably at least about 0.6, and even more suitably at least about 0.7, and still more suitably at least about 0.75. Where the dominant primary color of the graphic is yellow, the color density of the dominant primary color is at least about 0.5, more suitably at least about 0.55, and even more suitably at least about 0.6.

Color Density Test

The following test is used to determine the color density of the dominant primary color in a graphic applied to a non-woven substrate. The test involves using a reflectance densitometer, and more particularly a densitometer available from X-Rite, Inc. of Grandville, Mich., U.S.A. as model designation X-RITE 508 Densitometer. The densitometer is set for Status T measurement (which filters the density data in accordance with ANSI Status T Computerized Color Response) and for measuring the color density of the dominant primary color of a sample.

A sample non-woven substrate having a graphic applied thereto should be at least 6 mm in diameter (or in both length and width where the sample is non circular). The sample is placed on a white measuring tile (a 4 inch by 4 inch tile available from APT Tecko Company under the designation Deluxe White Marlite) and the densitometer is placed over the sample, with the cross-hairs of the densitometer sole plate positioned over the graphic. The nose of the densitometer is then held down against the sample until the display reads "Completed." The measured color density is displayed by the densitometer as a numeric value (dimensionless) preceded by a letter corresponding to the dominant primary color of the measured graphic; the letter Y referring to yellow, the letter M referring to magenta, the letter C referring to cyan, and the letter V referring to black.

At least three measurements should be taken and the results averaged to determine the color density of the sample being measured.

Experiment 1

An experiment was conducted to determine the effects of various parameters on the vibrancy (e.g., color density) of solid red and solid black square graphics applied to a laminate non-woven substrate. The parameters examined included the use of a thermally bonded laminate versus an adhesive bonded laminate; polyethylene fibers versus polypropylene fibers; ink compositions having an initial ink made by Sun Chemical Co. versus those having an initial ink made by Color Converting Industries (CCI) of Des Moines, Iowa, U.S.A.; anilox roll volume; and print plate material.

The tested parameters are more particularly set forth below.

Non-Woven Substrate Parameters
1. Substrate Construction
A. A laminate comprised of a spunbond fibrous non-woven web of 2.5 denier homofilament fibers composed of a polymer available from Exxon under the trade designation 3155 polymer, and a 0.5 weight percent $TiO_2$ additive. The fibrous non-woven web was point bonded in a wire weave bonding pattern. The fibrous non-woven web was also necked about 50 percent and had a necked basis weight of about 34 gsm. The film was a 19 gsm film available from Pliant under designation XP-8600. The fibrous non-woven web was adhesively bonded to the film using a 3 gsm basis weight adhesive available from Bostik-Findley under designation H2096.
B. A laminate comprised of a spunbond fibrous non-woven web of 2.5 denier bicomponent fibers having a 70 weight percent core of mPE available from Dow under the designation Affinity XUS59400 and a 30 weight percent sheath of PE available from Dow under the designation Aspun 6811A with an additive of 2 weight percent $TiO_2$. The fibrous non-woven web was point bonded over a 10 percent bond area. The film was a 19 gsm film available from Pliant under the designation XP-8600. The fibrous non-woven web was adhesively bonded to the film using a 3 gsm basis weight adhesive available from Bostik-Findley under designation H2096.
C. A laminate comprised of a spunbond fibrous non-woven web of 2.5 denier homofilament polypropylene fibers available from Union Carbide Corporation under the designation 5D49 PP, with a 0.75 weight percent $TiO_2$ additive. The web was point bonded in a wire weave 18 percent bond area pattern. The film was a microporous film comprised of an LLDPE available from Dow Chemical of Midland, Mich. under the designation Dowlex 2047 LLDPE, a calcium carbonate concentrate and a skin resin. The calcum carbonate concentrate was a blend of 75 weight percent calcium carbonate (available from OMYA, Inc., North America of Proctor, Vt. under the designation OMYACARB 2SST and having an average particle size of 2 micron, top cut of 8-10 microns and about 1% stearic acid coating), and 25 weight percent carrier resin (available from Dow Chemical under the designation Dowlex 2517 LLDPE an having a melt index of 25 g/10 min 190 C and density of 0.917 g/cc. The calcium carbonate concentrate was blended with the 2047 LLDPE in a single screw conventional extruder to obtain a final $CaCO_3$ concentration of about 49 weight percent. The skin resin was a combination of EVA's and catalloy, anti-oxidants, and process aid. The fibrous non-woven web was thermally laminated to the film.

Ink Composition Parameters
1. Ink Type
A. Available from Sun Chemical under the trade designation PYROFLEX; and
B. Available from CCI under model designation 1343 ink series.

Printing Apparatus Parameters
1. Print Method
A. stochastic;
B. standard dot process; and
C. line.
2. Anilox Roll Volume
A. 4.5 BCM (billion cubic microns);
B. 5.2 BCM;
C. 6.5 BCM;
D. 8.0 BCM; and
E. 10.0 BCM Note: the anilox roll volume as identified in the table attached as Appendix A is provided as two numbers (e.g., 260/5.2). The first number is the number of lines of cells per inch of width of the roller and the second number is the cell volume in billion cubic microns (BCM).

3. Plate Material
A. Available from BASF;
B. Available from E.I. duPont de Nemours Co. under the designation CYREL PQS; and
C. Available from E.I. duPont de Nemours Co. under the designation CYREL DPS.

Note: In the Appendix A table, the plate material is specified in terms of the plate material itself and the thickness of the plate at the raised portion thereof (e.g., 0.067 inches).

Set Parameters
Line speed: (e.g., speed at which substrate feeds through printing apparatus) 200 feet per minute.

Appendix A is a table identifying various test codes for this experiment and the parameters used for each test code. To prepare a test sample for a particular test code, the laminate non-woven substrate was made in accordance with the test code parameters. The ink composition (as specified for the particular test code) was supplied to the flexographic printing apparatus (which was configured and set for operation according to the test code). The laminate non-woven substrate was fed through the printing apparatus at the specified line speed and either red squares or black squares (depending on the test code) were imprinted onto the dry fibrous non-woven web of the substrate and allowed to dry. The Color Density Test described previously herein was performed on the graphic applied to the non-woven substrate to determine the color density of the dominant primary color of the graphic (in this instance, magenta or black depending on the test code).

The test codes set forth in the Appendix A table are identified by number and one of the letters A, B or C, with the letter corresponding to the particular non-woven substrate construction set forth above. Three samples were prepared for each test code, with the color density of each sample being measured three times. The results of the testing are also provided in the Appendix A table.

Experiment 2

A follow-on experiment was conducted to determine the effects of various parameters on the vibrancy (e.g., color density) of solid red square graphics applied to a laminate non-woven substrate. The parameters examined included the use of two different fibrous non-woven web constructions adhesively laminated to a film to form the laminate non-woven substrate; substrate treatment prior to printing, ink composition viscosity, solvent type, anilox roll volume, primer, print plate material, and impression pressure.

The tested parameters are more particularly set forth below.

Non-woven Substrate Parameters
1. Substrate Construction
A. A laminate comprised of a spunbond fibrous non-woven web of 2.5 denier homofilament fibers composed of a polymer available from Exxon under the designation 3155 polymer, with a 0.5 weight percent $TiO_2$ additive. The fibrous non-woven web was point bonded in a wire weave bonding pattern. The fibrous non-woven web was also necked about 50 percent and had a necked basis weight of about 34 gsm. The film was a 19 gsm film available from Pliant under designation XP-8600. The fibrous non-woven web was adhesively bonded to the film using a 3 gsm basis weight adhesive available from Bostik-Findley under designation H2096.
B. A laminate comprised of a spunbond fibrous non-woven web of 2.5 denier bicomponent fibers having a 70 weight percent core of mPE available from Dow under the designation Affinity XUS59400 and a 30 weight percent sheath of PE available from Dow under the designation Aspun 6811A with an additive of 2 weight percent $TiO_2$. The fibrous non-woven web was point bonded over a 10 percent bond area. The film was a 19 gsm film available from Pliant under the designation XP-8600. The fibrous non-woven web was adhesively bonded to the film using a 3 gsm basis weight adhesive available from Bostik-Findley under designation H2096.
Ink Composition Parameters
1. Ink Composition Viscosity (Print Ready)
A. 20 seconds as determined using a Zahn #2 cup;
B. 25 seconds as determined using a Zahn #2 cup;
C. 30 seconds as determined using a Zahn #2 cup; and
D. 35 seconds as determined using a Zahn #2 cup.
2. Ink Composition (Print Ready) Total Solvent Blend
A. 70 weight percent n-propyl alcohol and 30 weight percent n-propyl acetate; and
B. 50 weight percent propylene glycol n-propyl ether (PnP), 35 weight percent n-propyl alcohol and 15 weight percent n-propyl acetate.
Printing Apparatus Parameters
1. Plate Material
A. DuPont CYREL DPS;
B. natural rubber; and
C. DuPont CYREL DPS plate manufactured to have a textured printing surface containing a 200 line screen.
2. Primer
A. White primer as base for ink (underlying layer of white ink applied prior to applying ink composition).
B. None
3. Corona Treatment of Substrate
A. 3.1 kW
B. None
4. Impression Pressure
A. 0.115 inches ("low")
B. 0.125 inches ("high")
Set Parameters
Ink type: Available from Sun Chemical under the trade designation PYROFLEX.
Print method: line process.
Anilox Roll Volume: 6.5 BCM.
Line speed (e.g., speed at which substrate feeds through printing apparatus): 215 feet per minute.

Appendix B is a table identifying various test codes and the parameters used for each test code of this second experiment. To prepare a test sample for a particular test code, the laminate non-woven substrate was made in accordance with the test code parameters. The ink composition (as specified for the particular test code) was supplied to the flexographic printing apparatus (which was configured and set for operation according to the test code). The laminate non-woven substrate was fed through the printing apparatus at the specified line speed and red squares were imprinted onto the fibrous non-woven web of the substrate and allowed to dry. The Color Density Test described previously herein was performed on the graphic applied to the non-woven substrate to determine the color density of the dominant primary color of the graphic (in this instance, magenta).

Three samples were prepared for each test code, with the color density of each sample being measured three times. The results of the testing are also provided in the Appendix B table.

Experiment 3

A third experiment was conducted to determine the impact of various non-woven substrate parameters on the vibrancy (e.g., color density) of solid red square graphics applied to a laminate non-woven substrate. The parameters examined included the basis weight of the fibrous non-woven web of the substrate, the polyolefin from which the fibers were constructed, and whether or not the fibrous non-woven web was laminated to a backing layer.

The tested parameters are more particularly set forth below.

Non-woven fibrous web construction
All fibrous webs were point bonded over a 10 percent bond area.
1. Basis weight
A. 20 gsm (0.6 osy)
B. 34 gsm (1.0 osy)
2. Fiber Composition
All fibers were 2.5 denier bicomponent fibers having a sheath/core configuration in which the core comprised 70 weight percent mPE available from Dow Chemical under the designation Dow Affinity XUS59400. The sheath was one of the following:
A. 30 weight percent PE available from Dow Chemical under the designation Aspun 6811A; and
B. 30 weight percent PP available from Exxon under the designation 3155.
All sheaths had a 2 weight percent $TiO_2$ additive.
3. Laminate
A. None
B. The fibrous non-woven web was adhesively laminated to a 19 gsm film available from Pliant under the designation XP-8600, using 3 gsm adhesive available from Bostik-Findley under the designation H2096.

Set process parameters included:
Ink composition: available from Sun Chemical under the designation PYROFLEX.
Total Solvent Blend: 50 weight percent propylene glycol n-propyl ether (PnP), 35 weight percent n-propyl alcohol and 15 weight percent n-propyl acetate.
Ink composition viscosity: 25 seconds using a Zahn #2 cup.
Print plate material: DuPont CYREL DPS.

Appendix C is a table identifying the various parameter combinations for each test of this experiment. To prepare a test sample, the non-woven substrate was made in accordance with the test parameters. The ink composition was supplied to the flexographic printing apparatus and the non-woven substrate was fed through the printing apparatus whereby red squares were imprinted onto the fibrous non-woven web of the substrate and allowed to dry. The Color Density Test described previously herein was performed on the graphic applied to the non-woven substrate to determine the color density of the dominant primary color of the graphic (in this instance, magenta).

Three samples were prepared for each test code, with the color density of each sample being measured three times. The results of the testing are also provided in the Appendix C table.

Experiment 4

An experiment similar to Experiments 1-3 was conducted to determine the vibrancy (e.g., color density) of multi-color graphics wherein different regions of the graphic have different respective dominant primary colors. In particular, the overall graphic tested comprised multiple graphic images composed of multiple colors and was sized about 500 mm long by about 250 mm wide. The following three laminates were used in the experiment:

A. A laminate comprised of a spunbond fibrous non-woven web of 2.5 denier bicomponent fibers having a 70 weight percent core of mPE available from Dow under the designation Affinity XUS59400 and a 30 weight percent sheath of PE available from Dow under the designation Aspun 6811A with an additive of 2 weight percent $TiO_2$. The fibrous non-woven web was point bonded over a 10 percent bond area. The film was a 19 gsm film available from Pliant under the designation XP-8600. The fibrous non-woven web was adhesively bonded to the film using a 3 gsm basis weight sprayed adhesive available from Bostik-Findley under designation H2096.

B. A laminate comprised of a spunbond fibrous non-woven web of 2.5 denier homofilament polypropylene fibers available from Union Carbide Corporation under the designation 5D49 PP, with a 0.75 weight percent $TiO_2$ additive. The web was point bonded in a wire weave 18 percent bond area pattern. The film was a microporous film comprised of an LLDPE available from Dow Chemical of Midland, Mich. under the designation Dowlex 2047 LLDPE, a calcium carbonate concentrate and a skin resin. The calcum carbonate concentrate was a blend of 75 weight percent calcium carbonate (available from OMYA, Inc., North America of Proctor, Vt. under the designation OMYACARB 2SST and having an average particle size of 2 micron, top cut of 8-10 microns and about 1% stearic acid coating), and 25 weight percent carrier resin (available from Dow Chemical under the designation Dowlex 2517 LLDPE an having a melt index of 25 g/10 min 190 C and density of 0.917 g/cc. The calcium carbonate concentrate was blended with the 2047 LLDPE in a single screw conventional extruder to obtain a final $CaCO_3$ concentration of about 49 weight percent. The skin resin was a combination of EVA's and catalloy, anti-oxidants, and process aid. The fibrous non-woven web was thermally laminated to the film.

C. A laminate comprised of a spunbond fibrous non-woven web of 2.5 denier bicomponent fibers having a side-by-side configuration including 50 weight percent LLDPE available from Dow Chemical under the designation Dow 6811 and 50 weight percent PP available from Exxon under the designation 3155. The fibers also had a 0.5 weight percent $TiO_2$ additive. The fibrous non-woven web had a basis weight of about 20 gsm and was point bonded over a 10 percent bond area. The film was a 19 gsm film available from Pliant under the designation XP-8600. The fibrous non-woven web was adhesively bonded to the film using a 3 gsm basis weight sprayed adhesive available from Bostik-Findley under designation H2096.

The following set parameters were used in the experiment:
Ink Composition Parameters
Ink type: Available from Sun Chemical under the trade designation PYROFLEX.
Ink composition (print ready) total solvent blend: 50 weight percent propylene glycol n-propyl ether (PnP), 35 weight percent n-propyl alcohol and 15 weight percent n-propyl acetate.
Ink composition viscosity (print ready): 25 seconds as determined using a Zahn #2 cup;
Printing Apparatus Parameters
Plate material: DuPont CYREL DPS.
Print method: block.
Impression pressure: 0.115 inches.
Anilox roll volume: yellow: 200/8.0; blue 200/8.0; red 200/8.0; brown 260/5.2; black 200/6.3; Overprint varnish (ink binder with no pigment, e.g., clear ink—to improve rub resistance) 180/10.0.
Line speed: 170 feet per minute.

Appendix D is a table identifying the various tests conducted for this fourth experiment. For each laminate set forth above, the specified ink composition was supplied to the flexographic printing apparatus (which was configured and set for operation according to the set parameters). The laminate was fed through the printing apparatus at the specified line speed and multi-colored graphics were imprinted onto the fibrous non-woven web of the laminate and allowed to dry.

Figure 6B:
FIGS. 6a, 6b, 6c and 6d are respective portions of a multicolor graphic subjected to a Color Density Test to determine the color density of the dominant primary color of each respective portion of the graphic.
Figure 6D:
Figure 6A:
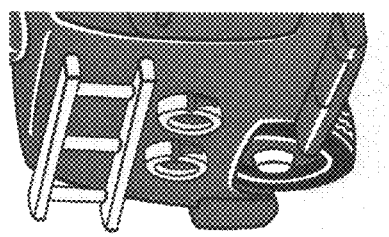
Figure 6C:

Four different regions of the overall graphic of each laminate were tested, with each region comprising a portion of the multi-colored graphic having a respective one of the four dominant primary colors (e.g., magenta from a generally red firetruck (FIG. 6a), cyan from a blue waist band image (FIG. 6b), black from a tire (FIG. 6c), or yellow from a character's shirt (FIG. 6d)). The Color Density Test described previously herein was performed on each sample to determine the color density of the dominant primary color of that portion of the graphic. The measurements were repeated for four additional laminates for each laminate type, at the same regions of the overall graphic, and the results were averaged to determine the color density for each dominant primary color. The results of the testing are provided in the Appendix D table.

Experiment 5—Comparison

A fifth experiment was conducted to determine the color density of graphics imprinted on non-woven substrates according to previously known processes. In particular, the following two samples were tested:

A. A multi-color block-printed graphic and non-woven polyproplylene substrate made in accordance with U.S. Pat. No. 5,458,590 (Schleinz et al.). More particularly, the ink composition was that set forth as ink formulation (C) of the '590 patent, including an ink purchased from Sun Chemical Co. under the designation PARABOND and a solvent blend of 75 percent by volume of ethylene glycol monopropyl ether and 25 percent by volume of n-propyl acetate. The viscosity of the ink composition (print ready) was about 25 seconds using a Zahn #2 cup.

B. A currently available multi-color block-printed graphic applied to a non-woven substrate used as a loop fastener material in HUGGIES ULTRATRIM DIAPERS (2004 production), commercially available from Kimberly-Clark Corporation of Neenah, Wis., U.S.A. (the substrate being otherwise commonly referred to as point unbonded loop material (PUB)). The graphic was comprised of an ink composition including Sun Chemical's PYROFLEX ink and a total solvent blend of 70 percent normal propyl alchol and 30 percent n-propyl acetate. The viscosity of the ink composition (print ready) was about 25 seconds using a Zahn #2 cup.

Four different regions of the overall graphic of each sample were tested, with each region comprising a portion of the multi-colored graphic having a respective one of the four dominant primary colors (e.g., magenta, cyan, black or yellow). The Color Density Test described previously herein was performed on each region to determine the color density of the dominant primary color of that region of the graphic. The measurements were repeated for four additional samples for each of the two sample types, at the same regions of the overall graphic, and the results were averaged to determine the color density for each dominant primary color. The results of the testing are provided in the Appendix E table.

Figure 4:
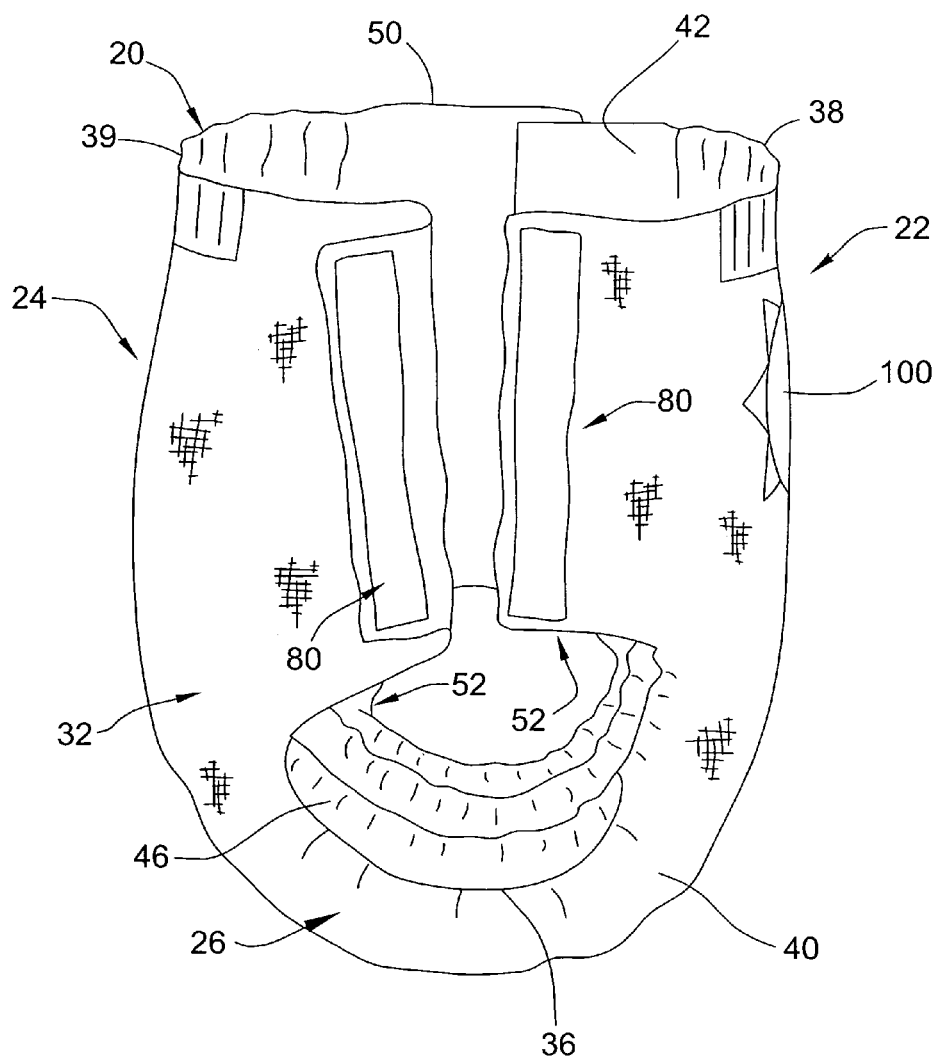
FIG. 4 is a side elevation of an absorbent article in the form of a pair of training pants incorporating the non-woven substrate of the present invention and shown in a partially unfastened condition.

The non-woven substrate having the high vibrancy graphic applied thereto may be useful by itself or as part of an absorbent article such as that illustrated in FIG. 4 in the form of children's toilet training pants and indicated in its entirety at 20. The absorbent article 20 may or may not be disposable, which refers to articles that are intended to be discarded after a limited period of use instead of being laundered or otherwise conditioned for reuse. It is understood that the non-woven substrate of the present invention having a graphic applied thereto is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

The pair of training pants 20 is illustrated in FIG. 4 in a partially fastened condition and define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The pants 20 also define an inner surface 28 adapted in use (e.g., positioned relative to the other components of the pants 20) to be disposed toward the wearer, and an outer surface 30 opposite the inner surface. The front and back waist regions 22, 24 comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pair of training pants 20 also has a pair of laterally opposite side edges 36 and a pair of longitudinally opposite waist edges (broadly, longitudinal ends), respectively designated front waist edge 38 and back waist edge 39.

The illustrated pants 20 comprises an absorbent assembly, generally indicated at 32, and a fastening system, generally indicated at 80, for securing the pants in a three-dimensional pants configuration. The absorbent assembly 32 comprises an outer cover 40 on which at least one high vibrancy graphic 100 of the present invention is applied and a bodyside liner 42 attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20. In addition, the liner 42 is suitably joined to the outer cover 40. The liner 42 is suitably adapted, i.e., positioned relative to the other components of the pants 20, for contiguous relationship with the wearer's skin during wear of the pants. The absorbent assembly 32 also comprises an absorbent structure (not shown) disposed between the outer cover 40 and the bodyside liner 42 for absorbing liquid body exudates exuded by the wearer and a pair of containment flaps 46 (one of which is indicated in FIG. 4) secured to the bodyside liner 42 for inhibiting the lateral flow of body exudates. Suitable constructions and arrangements for the containment flaps 46 are generally well known to those skilled in the art and are described in U.S. Pat. No. 4,704,116 issued Nov. 3, 1987 to Enloe, which is incorporated herein by reference.

With the training pants 20 in the fastened position as partially illustrated in FIG. 1, the front and back waist regions 22, 24 are connected together by the fastening system 80 to define the three-dimensional pants configuration having a waist opening 50 and a pair of leg openings 52. The front and back waist edges 38 and 39 (e.g. longitudinal ends) of the training pants 20 are configured to encircle the waist of the wearer to define the waist opening 50 (FIG. 1) of the pants.

The outer cover 40 (broadly defining a non-woven substrate according to one embodiment of the present invention) is suitably constructed in accordance with the construction of the non-woven substrate 200 as described previously and shown in FIGS. 1 and 2. In particular, the outer cover 40 suitably comprises a material that is substantially liquid impermeable. The outer cover 40 can be a single layer of liquid impermeable material, but more suitably comprises a multi-layered laminate structure in which at least one of the layers is liquid impermeable. For instance, the outer cover 40 can comprise a liquid permeable outer layer and a liquid impermeable inner layer that are suitably joined together by a laminate adhesive, ultrasonic bonds, thermal bonds, pressure bonds or the like. Suitable laminate adhesives, which can be applied continuously or intermittently as beads, a spray, parallel swirls, or the like, can be obtained from Bostik-Findley Adhesives, Inc., of Wauwautosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polyolefin nonwoven web. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.75 mil (0.02 millimeter) polyethylene film commercially available from Pliant Corporation of Schaumburg, Ill., U.S.A.

In another suitable embodiment, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond nonwoven fibrous web having a 0.7 osy (23.7 gsm) basis weight. The adhesive is similar to an adhesive which is supplied by Bostik-Findley Adhesive of Wauwautosa, Wis. and designated as H2525 A, and the elastomer strands are placed and distributed to provide approximately 12 strands of KRATON elastomer per inch (2.54 cm) of lateral width of the outer cover 40.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure. A suitable bodyside liner 42 may be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

Figure 5:
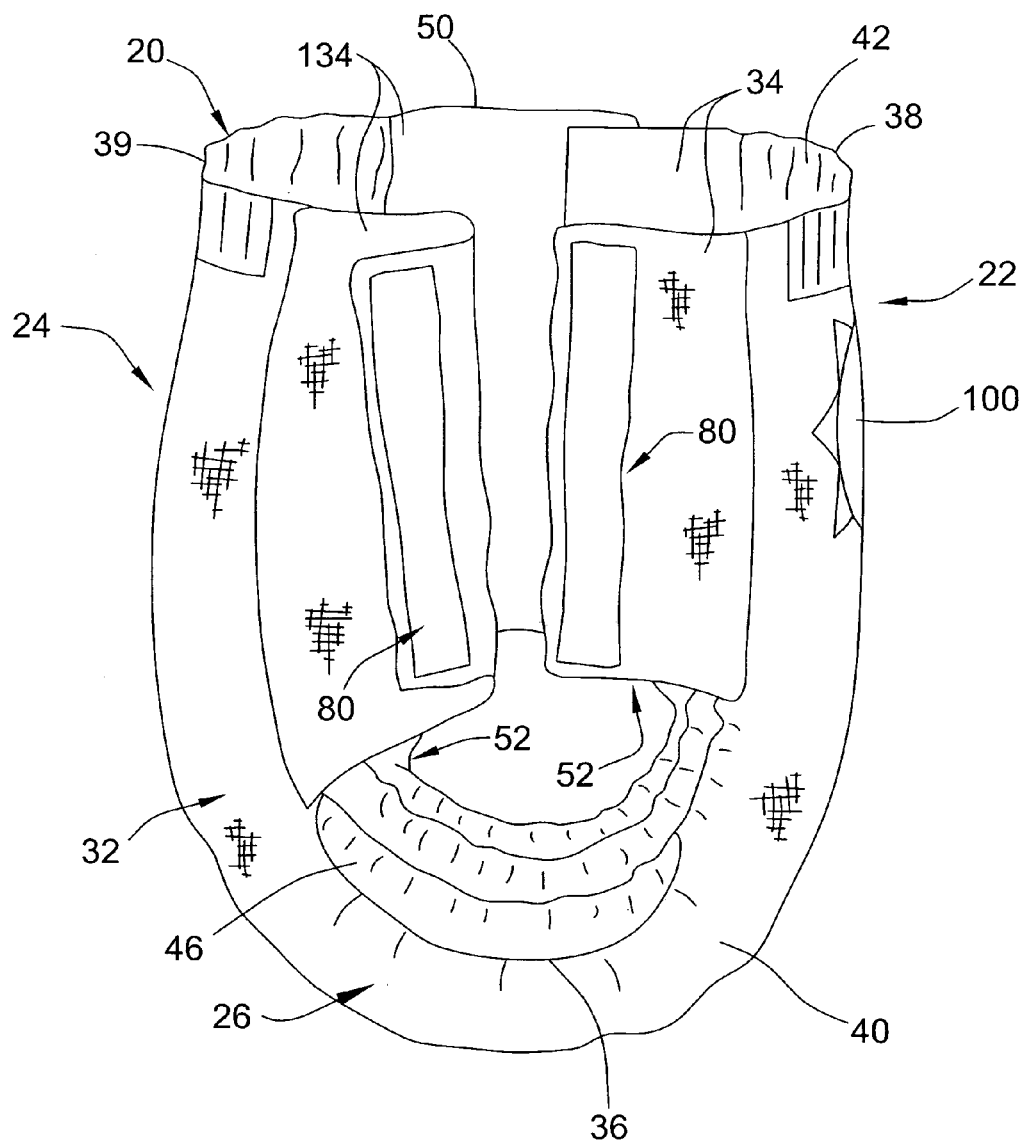
FIG. 5 is a side elevation of another embodiment of a pair of training pants incorporating the non-woven substrate of the present invention.

FIG. 5 illustrates another embodiment of the present invention wherein the absorbent article is the form of training pants 20 comprising a generally rectangular central absorbent assembly 32 and side panels 34, 134 formed separately from and secured to the central absorbent assembly. The side panels 34, 134 are permanently bonded to the central absorbent assembly 32 in the respective front and back waist regions 22 and 24 of the pants 20. More particularly, the front side panels 34 can be permanently bonded to and extend transversely outward beyond the side margins of the absorbent assembly 32 at the front waist region 22, and the back side panels 134 can be permanently bonded to and extend transversely outward beyond the side margins of the absorbent assembly at the back waist region 24. The side panels 34 and 134 may be bonded to the absorbent assembly 32 using attachment means known to those skilled in the art such as adhesive, thermal or ultrasonic bonding.

The front and back side panels 34 and 134, upon wearing of the pants 20, thus comprise the portions of the training pants 20 which are positioned on the hips of the wearer. The front and back side panels 34 and 134 can be permanently bonded together to form the three-dimensional configuration of the pants 20, or be releasably connected with one another such as by the fastening system 80 of the illustrated aspects.

In the embodiment of FIG. 5, the side panels 34, 134 comprise an elastic material capable of stretching at least in a direction generally parallel to the lateral direction of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may include other woven or non-woven materials, such as those described herein as being suitable for construction of the outer cover 40 and/or the bodyside liner 42; mechanically pre-strained composites; or stretchable but inelastic materials.

In the illustrated embodiments of FIGS. 4 and 5, the outer cover of the pants 20 broadly defines the non-woven substrate having a high vibrancy graphic applied thereto. However, it is understood that a high vibrancy graphic may instead, or may additionally, be applied to other non-woven substrate components of the pants 20, such as the bodyside liner 42 or other components, and remain within the scope of this invention.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements

APPENDIX A

Print Vibrancy - Trial 1

| Code | Material | Color | Plate Mat. | Anilox | Method | Ink | Sample | Result 1 | Result 2 | Result 3 |
|---|---|---|---|---|---|---|---|---|---|---|
| 1 | A | Red | DPS .067" | 260 5.2 | Process | Sun | 1 | 44 | 47 | 48 |
| 1 | A | Red | DPS .067" | 260 5.2 | Process | Sun | 2 | 50 | 48 | 49 |
| 1 | A | Red | DPS .067" | 260 5.2 | Process | Sun | 3 | 48 | 44 | 49 |
| 1 | B | Red | DPS .067" | 260 5.2 | Process | Sun | 1 | 54 | 56 | 55 |
| 1 | B | Red | DPS .067" | 260 5.2 | Process | Sun | 2 | 53 | 63 | 53 |
| 1 | B | Red | DPS .067" | 260 5.2 | Process | Sun | 3 | 60 | 60 | 68 |
| 1 | C | Red | DPS .067" | 260 5.2 | Process | Sun | 1 | 61 | 42 | 41 |
| 1 | C | Red | DPS .067" | 260 5.2 | Process | Sun | 2 | 48 | 43 | 50 |
| 1 | C | Red | DPS .067" | 260 5.2 | Process | Sun | 3 | 54 | 40 | 42 |
| 2 | A | Red | DPS .067" | 360 4.5 | Process | Sun | 1 | 53 | 54 | 51 |
| 2 | A | Red | DPS .067" | 360 4.5 | Process | Sun | 2 | 48 | 54 | 56 |
| 2 | A | Red | DPS .067" | 360 4.5 | Process | Sun | 3 | 57 | 55 | 54 |
| 2 | B | Red | DPS .067" | 360 4.5 | Process | Sun | 1 | 59 | 63 | 67 |
| 2 | B | Red | DPS .067" | 360 4.5 | Process | Sun | 2 | 61 | 60 | 56 |
| 2 | B | Red | DPS .067" | 360 4.5 | Process | Sun | 3 | 64 | 57 | 61 |
| 2 | C | Red | DPS .067" | 360 4.5 | Process | Sun | 1 | 50 | 55 | 47 |
| 2 | C | Red | DPS .067" | 360 4.5 | Process | Sun | 2 | 49 | 59 | 61 |
| 2 | C | Red | DPS .067" | 360 4.5 | Process | Sun | 3 | 48 | 52 | 56 |
| 3 | A | Red | BASF .067" | 260 5.2 | Process | Sun | 1 | 46 | 52 | 52 |
| 3 | A | Red | BASF .067" | 260 5.2 | Process | Sun | 2 | 51 | 51 | 53 |
| 3 | A | Red | BASF .067" | 260 5.2 | Process | Sun | 3 | 46 | 56 | 48 |
| 3 | B | Red | BASF .067" | 260 5.2 | Process | Sun | 1 | 65 | 59 | 62 |
| 3 | B | Red | BASF .067" | 260 5.2 | Process | Sun | 2 | 59 | 64 | 57 |
| 3 | B | Red | BASF .067" | 260 5.2 | Process | Sun | 3 | 57 | 51 | 65 |
| 3 | C | Red | BASF .067" | 260 5.2 | Process | Sun | 1 | 52 | 47 | 59 |
| 3 | C | Red | BASF .067" | 260 5.2 | Process | Sun | 2 | 47 | 56 | 49 |
| 3 | C | Red | BASF .067" | 260 5.2 | Process | Sun | 3 | 47 | 47 | 64 |
| 4 | A | Red | BASF .067" | 360 4.5 | Process | Sun | 1 | 41 | 46 | 46 |
| 4 | A | Red | BASF .067" | 360 4.5 | Process | Sun | 2 | 42 | 46 | 44 |
| 4 | A | Red | BASF .067" | 360 4.5 | Process | Sun | 3 | 41 | 40 | 46 |
| 4 | B | Red | BASF .067" | 360 4.5 | Process | Sun | 1 | 54 | 68 | 59 |
| 4 | B | Red | BASF .067" | 360 4.5 | Process | Sun | 2 | 50 | 64 | 56 |
| 4 | B | Red | BASF .067" | 360 4.5 | Process | Sun | 3 | 60 | 66 | 63 |
| 4 | C | Red | BASF .067" | 360 4.5 | Process | Sun | 1 | 51 | 47 | 49 |
| 4 | C | Red | BASF .067" | 360 4.5 | Process | Sun | 2 | 57 | 50 | 56 |
| 4 | C | Red | BASF .067" | 360 4.5 | Process | Sun | 3 | 45 | 45 | 52 |
| 5 | A | Red | DPS .067" | 260 5.2 | Stochastic | Sun | 1 | 51 | 52 | 52 |
| 5 | A | Red | DPS .067" | 260 5.2 | Stochastic | Sun | 2 | 55 | 44 | 53 |
| 5 | A | Red | DPS .067" | 260 5.2 | Stochastic | Sun | 3 | 49 | 43 | 49 |
| 5 | B | Red | DPS .067" | 260 5.2 | Stochastic | Sun | 1 | 52 | 56 | 59 |
| 5 | B | Red | DPS .067" | 260 5.2 | Stochastic | Sun | 2 | 55 | 56 | 61 |
| 5 | B | Red | DPS .067" | 260 5.2 | Stochastic | Sun | 3 | 60 | 58 | 61 |
| 5 | C | Red | DPS .067" | 260 5.2 | Stochastic | Sun | 1 | 56 | 42 | 52 |
| 5 | C | Red | DPS .067" | 260 5.2 | Stochastic | Sun | 2 | 47 | 59 | 58 |
| 5 | C | Red | DPS .067" | 260 5.2 | Stochastic | Sun | 3 | 51 | 56 | 48 |
| 6 | A | Red | DPS .067" | 360 4.5 | Stochastic | Sun | 1 | 42 | 46 | 47 |
| 6 | A | Red | DPS .067" | 360 4.5 | Stochastic | Sun | 2 | 42 | 47 | 42 |
| 6 | A | Red | DPS .067" | 360 4.5 | Stochastic | Sun | 3 | 42 | 47 | 40 |
| 6 | B | Red | DPS .067" | 360 4.5 | Stochastic | Sun | 1 | 58 | 48 | 48 |
| 6 | B | Red | DPS .067" | 360 4.5 | Stochastic | Sun | 2 | 55 | 53 | 60 |
| 6 | B | Red | DPS .067" | 360 4.5 | Stochastic | Sun | 3 | 64 | 54 | 49 |
| 6 | C | Red | DPS .067" | 360 4.5 | Stochastic | Sun | 1 | 64 | 50 | 46 |
| 6 | C | Red | DPS .067" | 360 4.5 | Stochastic | Sun | 2 | 54 | 59 | 50 |
| 6 | C | Red | DPS .067" | 360 4.5 | Stochastic | Sun | 3 | 52 | 66 | 63 |
| 7 | A | Red | BASF .067" | 260 5.2 | Stochastic | Sun | 1 | 37 | 33 | 46 |
| 7 | A | Red | BASF .067" | 260 5.2 | Stochastic | Sun | 2 | 40 | 38 | 37 |
| 7 | A | Red | BASF .067" | 260 5.2 | Stochastic | Sun | 3 | 46 | 37 | 42 |
| 7 | B | Red | BASF .067" | 260 5.2 | Stochastic | Sun | 1 | 40 | 39 | 34 |
| 7 | B | Red | BASF .067" | 260 5.2 | Stochastic | Sun | 2 | 38 | 41 | 38 |
| 7 | B | Red | BASF .067" | 260 5.2 | Stochastic | Sun | 3 | 32 | 40 | 44 |
| 7 | C | Red | BASF .067" | 260 5.2 | Stochastic | Sun | 1 | 43 | 44 | 51 |
| 7 | C | Red | BASF .067" | 260 5.2 | Stochastic | Sun | 2 | 62 | 42 | 59 |
| 7 | C | Red | BASF .067" | 260 5.2 | Stochastic | Sun | 3 | 51 | 43 | 39 |
| 8 | A | Red | BASF .067" | 360 4.5 | Stochastic | Sun | 1 | 52 | 52 | 51 |
| 8 | A | Red | BASF .067" | 360 4.5 | Stochastic | Sun | 2 | 53 | 52 | 55 |
| 8 | A | Red | BASF .067" | 360 4.5 | Stochastic | Sun | 3 | 52 | 56 | 55 |
| 8 | B | Red | BASF .067" | 360 4.5 | Stochastic | Sun | 1 | 61 | 60 | 57 |
| 8 | B | Red | BASF .067" | 360 4.5 | Stochastic | Sun | 2 | 61 | 62 | 63 |
| 8 | B | Red | BASF .067" | 360 4.5 | Stochastic | Sun | 3 | 67 | 62 | 65 |
| 8 | C | Red | BASF .067" | 360 4.5 | Stochastic | Sun | 1 | 52 | 59 | 56 |
| 8 | C | Red | BASF .067" | 360 4.5 | Stochastic | Sun | 2 | 66 | 46 | 64 |
| 8 | C | Red | BASF .067" | 360 4.5 | Stochastic | Sun | 3 | 50 | 59 | 63 |
| 17 | A | Black | DPS .067" | 260 5.2 | Process | Sun | 1 | 52 | 49 | 53 |

-continued

| | | | | | Print Vibrancy - Trial 1 | | | | | |
|---|---|---|---|---|---|---|---|---|---|---|
| Code | Material | Color | Plate Mat. | Anilox | Method | Ink | Sample | Result 1 | Result 2 | Result 3 |
| 17 | A | Black | DPS .067" | 260 5.2 | Process | Sun | 2 | 47 | 45 | 53 |
| 17 | A | Black | DPS .067" | 260 5.2 | Process | Sun | 3 | 41 | 51 | 58 |
| 17 | B | Black | DPS .067" | 260 5.2 | Process | Sun | 1 | 68 | 63 | 63 |
| 17 | B | Black | DPS .067" | 260 5.2 | Process | Sun | 2 | 67 | 60 | 62 |
| 17 | B | Black | DPS .067" | 260 5.2 | Process | Sun | 3 | 63 | 64 | 56 |
| 17 | C | Black | DPS .067" | 260 5.2 | Process | Sun | 1 | 69 | 57 | 54 |
| 17 | C | Black | DPS .067" | 260 5.2 | Process | Sun | 2 | 55 | 51 | 67 |
| 17 | C | Black | DPS .067" | 260 5.2 | Process | Sun | 3 | 52 | 51 | 71 |
| 18 | A | Black | DPS .067" | 360 4.5 | Process | Sun | 1 | 49 | 51 | 46 |
| 18 | A | Black | DPS .067" | 360 4.5 | Process | Sun | 2 | 49 | 49 | 49 |
| 18 | A | Black | DPS .067" | 360 4.5 | Process | Sun | 3 | 46 | 48 | 47 |
| 18 | B | Black | DPS .067" | 360 4.5 | Process | Sun | 1 | 52 | 55 | 54 |
| 18 | B | Black | DPS .067" | 360 4.5 | Process | Sun | 2 | 55 | 60 | 61 |
| 18 | B | Black | DPS .067" | 360 4.5 | Process | Sun | 3 | 58 | 61 | 59 |
| 18 | C | Black | DPS .067" | 360 4.5 | Process | Sun | 1 | 42 | 61 | 58 |
| 18 | C | Black | DPS .067" | 360 4.5 | Process | Sun | 2 | 42 | 63 | 51 |
| 18 | C | Black | DPS .067" | 360 4.5 | Process | Sun | 3 | 45 | 46 | 43 |
| 19 | A | Black | BASF .067" | 260 5.2 | Process | Sun | 1 | 42 | 48 | 48 |
| 19 | A | Black | BASF .067" | 260 5.2 | Process | Sun | 2 | 39 | 51 | 50 |
| 19 | A | Black | BASF .067" | 260 5.2 | Process | Sun | 3 | 45 | 45 | 45 |
| 19 | B | Black | BASF .067" | 260 5.2 | Process | Sun | 1 | 49 | 55 | 60 |
| 19 | B | Black | BASF .067" | 260 5.2 | Process | Sun | 2 | 60 | 57 | 57 |
| 19 | B | Black | BASF .067" | 260 5.2 | Process | Sun | 3 | 42 | 57 | 56 |
| 19 | C | Black | BASF .067" | 260 5.2 | Process | Sun | 1 | 48 | 48 | 52 |
| 19 | C | Black | BASF .067" | 260 5.2 | Process | Sun | 2 | 44 | 47 | 45 |
| 19 | C | Black | BASF .067" | 260 5.2 | Process | Sun | 3 | 47 | 45 | 46 |
| 20 | A | Black | BASF .067" | 360 4.5 | Process | Sun | 1 | 35 | 42 | 36 |
| 20 | A | Black | BASF .067" | 360 4.5 | Process | Sun | 2 | 42 | 36 | 37 |
| 20 | A | Black | BASF .067" | 360 4.5 | Process | Sun | 3 | 37 | 37 | 46 |
| 20 | B | Black | BASF .067" | 360 4.5 | Process | Sun | 1 | 50 | 58 | 54 |
| 20 | B | Black | BASF .067" | 360 4.5 | Process | Sun | 2 | 58 | 58 | 48 |
| 20 | B | Black | BASF .067" | 360 4.5 | Process | Sun | 3 | 55 | 57 | 55 |
| 20 | C | Black | BASF .067" | 360 4.5 | Process | Sun | 1 | 41 | 54 | 43 |
| 20 | C | Black | BASF .067" | 360 4.5 | Process | Sun | 2 | 43 | 39 | 39 |
| 20 | C | Black | BASF .067" | 360 4.5 | Process | Sun | 3 | 48 | 51 | 41 |
| 21 | A | Black | DPS .067" | 260 5.2 | Stochastic | Sun | 1 | 59 | 58 | 57 |
| 21 | A | Black | DPS .067" | 260 5.2 | Stochastic | Sun | 2 | 60 | 56 | 57 |
| 21 | A | Black | DPS .067" | 260 5.2 | Stochastic | Sun | 3 | 57 | 56 | 61 |
| 21 | B | Black | DPS .067" | 260 5.2 | Stochastic | Sun | 1 | 61 | 59 | 65 |
| 21 | B | Black | DPS .067" | 260 5.2 | Stochastic | Sun | 2 | 59 | 66 | 74 |
| 21 | B | Black | DPS .067" | 260 5.2 | Stochastic | Sun | 3 | 64 | 67 | 67 |
| 21 | C | Black | DPS .067" | 260 5.2 | Stochastic | Sun | 1 | 52 | 54 | 54 |
| 21 | C | Black | DPS .067" | 260 5.2 | Stochastic | Sun | 2 | 51 | 51 | 54 |
| 21 | C | Black | DPS .067" | 260 5.2 | Stochastic | Sun | 3 | 47 | 54 | 54 |
| 22 | A | Black | DPS .067" | 360 4.5 | Stochastic | Sun | 1 | 56 | 56 | 55 |
| 22 | A | Black | DPS .067" | 360 4.5 | Stochastic | Sun | 2 | 52 | 56 | 54 |
| 22 | A | Black | DPS .067" | 360 4.5 | Stochastic | Sun | 3 | 52 | 52 | 51 |
| 22 | B | Black | DPS .067" | 360 4.5 | Stochastic | Sun | 1 | 63 | 60 | 67 |
| 22 | B | Black | DPS .067" | 360 4.5 | Stochastic | Sun | 2 | 60 | 59 | 57 |
| 22 | B | Black | DPS .067" | 360 4.5 | Stochastic | Sun | 3 | 68 | 62 | 63 |
| 22 | C | Black | DPS .067" | 360 4.5 | Stochastic | Sun | 1 | 59 | 61 | 63 |
| 22 | C | Black | DPS .067" | 360 4.5 | Stochastic | Sun | 2 | 53 | 49 | 49 |
| 22 | C | Black | DPS .067" | 360 4.5 | Stochastic | Sun | 3 | 50 | 53 | 54 |
| 23 | A | Black | BASF .067" | 260 5.2 | Stochastic | Sun | 1 | 49 | 55 | 57 |
| 23 | A | Black | BASF .067" | 260 5.2 | Stochastic | Sun | 2 | 54 | 50 | 53 |
| 23 | A | Black | BASF .067" | 260 5.2 | Stochastic | Sun | 3 | 50 | 60 | 54 |
| 23 | B | Black | BASF .067" | 260 5.2 | Stochastic | Sun | 1 | 63 | 58 | 55 |
| 23 | B | Black | BASF .067" | 260 5.2 | Stochastic | Sun | 2 | 58 | 51 | 63 |
| 23 | B | Black | BASF .067" | 260 5.2 | Stochastic | Sun | 3 | 65 | 58 | 70 |
| 23 | C | Black | BASF .067" | 260 5.2 | Stochastic | Sun | 1 | 53 | 51 | 69 |
| 23 | C | Black | BASF .067" | 260 5.2 | Stochastic | Sun | 2 | 46 | 60 | 60 |
| 23 | C | Black | BASF .067" | 260 5.2 | Stochastic | Sun | 3 | 48 | 60 | 58 |
| 24 | A | Black | BASF .067" | 360 4.5 | Stochastic | Sun | 1 | 52 | 45 | 50 |
| 24 | A | Black | BASF .067" | 360 4.5 | Stochastic | Sun | 2 | 49 | 54 | 46 |
| 24 | A | Black | BASF .067" | 360 4.5 | Stochastic | Sun | 3 | 49 | 48 | 54 |
| 24 | B | Black | BASF .067" | 360 4.5 | Stochastic | Sun | 1 | 66 | 67 | 57 |
| 24 | B | Black | BASF .067" | 360 4.5 | Stochastic | Sun | 2 | 62 | 67 | 50 |
| 24 | B | Black | BASF .067" | 360 4.5 | Stochastic | Sun | 3 | 55 | 69 | 59 |
| 24 | C | Black | BASF .067" | 360 4.5 | Stochastic | Sun | 1 | 50 | 45 | 51 |
| 24 | C | Black | BASF .067" | 360 4.5 | Stochastic | Sun | 2 | 49 | 48 | 48 |
| 24 | C | Black | BASF .067" | 360 4.5 | Stochastic | Sun | 3 | 53 | 53 | 47 |
| 33 | A | Black | PQS .067" | 180 10.0 | Line | Sun | 1 | 59 | 49 | 47 |
| 33 | A | Black | PQS .067" | 180 10.0 | Line | Sun | 2 | 62 | 54 | 57 |
| 33 | A | Black | PQS .067" | 180 10.0 | Line | Sun | 3 | 64 | 59 | 58 |
| 33 | B | Black | PQS .067" | 180 10.0 | Line | Sun | 1 | 67 | 70 | 76 |
| 33 | B | Black | PQS .067" | 180 10.0 | Line | Sun | 2 | 71 | 66 | 70 |

-continued

| | | | | | Print Vibrancy - Trial 1 | | | | | |
|---|---|---|---|---|---|---|---|---|---|---|
| Code | Material | Color | Plate Mat. | Anilox | Method | Ink | Sample | Result 1 | Result 2 | Result 3 |
| 33 | B | Black | PQS .067" | 180 10.0 | Line | Sun | 3 | 62 | 49 | 66 |
| 33 | C | Black | PQS .067" | 180 10.0 | Line | Sun | 1 | 47 | 51 | 54 |
| 33 | C | Black | PQS .067" | 180 10.0 | Line | Sun | 2 | 51 | 47 | 50 |
| 33 | C | Black | PQS .067" | 180 10.0 | Line | Sun | 3 | 40 | 54 | 64 |
| 34 | A | Black | PQS .067" | 200 8.0 | Line | Sun | 1 | 60 | 55 | 54 |
| 34 | A | Black | PQS .067" | 200 8.0 | Line | Sun | 2 | 51 | 50 | 45 |
| 34 | A | Black | PQS .067" | 200 8.0 | Line | Sun | 3 | 54 | 56 | 59 |
| 34 | B | Black | PQS .067" | 200 8.0 | Line | Sun | 1 | 75 | 63 | 66 |
| 34 | B | Black | PQS .067" | 200 8.0 | Line | Sun | 2 | 73 | 66 | 73 |
| 34 | B | Black | PQS .067" | 200 8.0 | Line | Sun | 3 | 75 | 72 | 64 |
| 34 | C | Black | PQS .067" | 200 8.0 | Line | Sun | 1 | 53 | 67 | 65 |
| 34 | C | Black | PQS .067" | 200 8.0 | Line | Sun | 2 | 54 | 60 | 66 |
| 34 | C | Black | PQS .067" | 200 8.0 | Line | Sun | 3 | 55 | 67 | 60 |
| 35 | A | Black | PQS .067" | 240 6.5 | Line | Sun | 1 | 62 | 53 | 55 |
| 35 | A | Black | PQS .067" | 240 6.5 | Line | Sun | 2 | 50 | 54 | 59 |
| 35 | A | Black | PQS .067" | 240 6.5 | Line | Sun | 3 | 58 | 55 | 57 |
| 35 | B | Black | PQS .067" | 240 6.5 | Line | Sun | 1 | 58 | 63 | 76 |
| 35 | B | Black | PQS .067" | 240 6.5 | Line | Sun | 2 | 76 | 72 | 69 |
| 35 | B | Black | PQS .067" | 240 6.5 | Line | Sun | 3 | 70 | 65 | 73 |
| 35 | C | Black | PQS .067" | 240 6.5 | Line | Sun | 1 | 55 | 52 | 55 |
| 35 | C | Black | PQS .067" | 240 6.5 | Line | Sun | 2 | 55 | 51 | 54 |
| 35 | C | Black | PQS .067" | 240 6.5 | Line | Sun | 3 | 53 | 65 | 60 |
| 36 | A | Black | PQS .067" | 360 4.5 | Line | Sun | 1 | 38 | 35 | 45 |
| 36 | A | Black | PQS .067" | 360 4.5 | Line | Sun | 2 | 33 | 39 | 34 |
| 36 | A | Black | PQS .067" | 360 4.5 | Line | Sun | 3 | 34 | 44 | 40 |
| 36 | B | Black | PQS .067" | 360 4.5 | Line | Sun | 1 | 54 | 49 | 51 |
| 36 | B | Black | PQS .067" | 360 4.5 | Line | Sun | 2 | 54 | 49 | 57 |
| 36 | B | Black | PQS .067" | 360 4.5 | Line | Sun | 3 | 51 | 58 | 45 |
| 36 | C | Black | PQS .067" | 360 4.5 | Line | Sun | 1 | 43 | 47 | 48 |
| 36 | C | Black | PQS .067" | 360 4.5 | Line | Sun | 2 | 35 | 49 | 51 |
| 36 | C | Black | PQS .067" | 360 4.5 | Line | Sun | 3 | 38 | 39 | 34 |
| 41 | A | Red | DPS .067" | 260 5.2 | Process | CCI | 1 | 57 | 49 | 53 |
| 41 | A | Red | DPS .067" | 260 5.2 | Process | CCI | 2 | 52 | 58 | 55 |
| 41 | A | Red | DPS .067" | 260 5.2 | Process | CCI | 3 | 50 | 51 | 53 |
| 41 | B | Red | DPS .067" | 260 5.2 | Process | CCI | 1 | 59 | 55 | 60 |
| 41 | B | Red | DPS .067" | 260 5.2 | Process | CCI | 2 | 60 | 57 | 59 |
| 41 | B | Red | DPS .067" | 260 5.2 | Process | CCI | 3 | 62 | 55 | 55 |
| 41 | C | Red | DPS .067" | 260 5.2 | Process | CCI | 1 | 65 | 51 | 55 |
| 41 | C | Red | DPS .067" | 260 5.2 | Process | CCI | 2 | 44 | 51 | 50 |
| 41 | C | Red | DPS .067" | 260 5.2 | Process | CCI | 3 | 61 | 54 | 55 |
| 42 | A | Red | DPS .067" | 360 4.5 | Process | CCI | 1 | 54 | 52 | 52 |
| 42 | A | Red | DPS .067" | 360 4.5 | Process | CCI | 2 | 52 | 52 | 53 |
| 42 | A | Red | DPS .067" | 360 4.5 | Process | CCI | 3 | 54 | 56 | 54 |
| 42 | B | Red | DPS .067" | 360 4.5 | Process | CCI | 1 | 57 | 59 | 59 |
| 42 | B | Red | DPS .067" | 360 4.5 | Process | CCI | 2 | 60 | 56 | 58 |
| 42 | B | Red | DPS .067" | 360 4.5 | Process | CCI | 3 | 59 | 60 | 59 |
| 42 | C | Red | DPS .067" | 360 4.5 | Process | CCI | 1 | 48 | 58 | 58 |
| 42 | C | Red | DPS .067" | 360 4.5 | Process | CCI | 2 | 54 | 49 | 56 |
| 42 | C | Red | DPS .067" | 360 4.5 | Process | CCI | 3 | 62 | 48 | 58 |
| 51 | A | Red | BASF .067" | 260 5.2 | Process | CCI | 1 | 50 | 43 | 47 |
| 51 | A | Red | BASF .067" | 260 5.2 | Process | CCI | 2 | 44 | 41 | 45 |
| 51 | A | Red | BASF .067" | 260 5.2 | Process | CCI | 3 | 46 | 51 | 47 |
| 51 | B | Red | BASF .067" | 260 5.2 | Process | CCI | 1 | 55 | 52 | 51 |
| 51 | B | Red | BASF .067" | 260 5.2 | Process | CCI | 2 | 60 | 54 | 53 |
| 51 | B | Red | BASF .067" | 260 5.2 | Process | CCI | 3 | 59 | 61 | 58 |
| 51 | C | Red | BASF .067" | 260 5.2 | Process | CCI | 1 | 47 | 53 | 55 |
| 51 | C | Red | BASF .067" | 260 5.2 | Process | CCI | 2 | 50 | 51 | 44 |
| 51 | C | Red | BASF .067" | 260 5.2 | Process | CCI | 3 | 41 | 54 | 51 |
| 52 | A | Red | BASF .067" | 360 4.5 | Process | CCI | 1 | 52 | 50 | 50 |
| 52 | A | Red | BASF .067" | 360 4.5 | Process | CCI | 2 | 52 | 47 | 49 |
| 52 | A | Red | BASF .067" | 360 4.5 | Process | CCI | 3 | 48 | 50 | 48 |
| 52 | B | Red | BASF .067" | 360 4.5 | Process | CCI | 1 | 56 | 56 | 58 |
| 52 | B | Red | BASF .067" | 360 4.5 | Process | CCI | 2 | 58 | 59 | 52 |
| 52 | B | Red | BASF .067" | 360 4.5 | Process | CCI | 3 | 49 | 57 | 57 |
| 52 | C | Red | BASF .067" | 360 4.5 | Process | CCI | 1 | 51 | 49 | 56 |
| 52 | C | Red | BASF .067" | 360 4.5 | Process | CCI | 2 | 54 | 50 | 44 |
| 52 | C | Red | BASF .067" | 360 4.5 | Process | CCI | 3 | 55 | 60 | 56 |
| 45 | A | Red | DPS .067" | 260 5.2 | Stochastic | CCI | 1 | 50 | 56 | 54 |
| 45 | A | Red | DPS .067" | 260 5.2 | Stochastic | CCI | 2 | 53 | 57 | 52 |
| 45 | A | Red | DPS .067" | 260 5.2 | Stochastic | CCI | 3 | 50 | 55 | 52 |
| 45 | B | Red | DPS .067" | 260 5.2 | Stochastic | CCI | 1 | 58 | 61 | 59 |
| 45 | B | Red | DPS .067" | 260 5.2 | Stochastic | CCI | 2 | 60 | 59 | 60 |
| 45 | B | Red | DPS .067" | 260 5.2 | Stochastic | CCI | 3 | 63 | 66 | 64 |
| 45 | C | Red | DPS .067" | 260 5.2 | Stochastic | CCI | 1 | 55 | 64 | 49 |
| 45 | C | Red | DPS .067" | 260 5.2 | Stochastic | CCI | 2 | 46 | 55 | 55 |
| 45 | C | Red | DPS .067" | 260 5.2 | Stochastic | CCI | 3 | 48 | 47 | 52 |

-continued

| | | | | | Print Vibrancy - Trial 1 | | | | |
|---|---|---|---|---|---|---|---|---|---|---|
| Code | Material | Color | Plate Mat. | Anilox | Method | Ink | Sample | Result 1 | Result 2 | Result 3 |
| 46 | A | Red | DPS .067" | 360 4.5 | Stochastic | CCI | 1 | 52 | 50 | 48 |
| 46 | A | Red | DPS .067" | 360 4.5 | Stochastic | CCI | 2 | 50 | 51 | 48 |
| 46 | A | Red | DPS .067" | 360 4.5 | Stochastic | CCI | 3 | 53 | 50 | 52 |
| 46 | B | Red | DPS .067" | 360 4.5 | Stochastic | CCI | 1 | 57 | 58 | 60 |
| 46 | B | Red | DPS .067" | 360 4.5 | Stochastic | CCI | 2 | 56 | 59 | 53 |
| 46 | B | Red | DPS .067" | 360 4.5 | Stochastic | CCI | 3 | 53 | 59 | 56 |
| 46 | C | Red | DPS .067" | 360 4.5 | Stochastic | CCI | 1 | 48 | 52 | 46 |
| 46 | C | Red | DPS .067" | 360 4.5 | Stochastic | CCI | 2 | 47 | 55 | 56 |
| 46 | C | Red | DPS .067" | 360 4.5 | Stochastic | CCI | 3 | 47 | 48 | 50 |
| 53 | A | Red | BASF .067" | 260 5.2 | Stochastic | CCI | 1 | 46 | 43 | 48 |
| 53 | A | Red | BASF .067" | 260 5.2 | Stochastic | CCI | 2 | 46 | 40 | 53 |
| 53 | A | Red | BASF .067" | 260 5.2 | Stochastic | CCI | 3 | 49 | 39 | 47 |
| 53 | B | Red | BASF .067" | 260 5.2 | Stochastic | CCI | 1 | 55 | 50 | 53 |
| 53 | B | Red | BASF .067" | 260 5.2 | Stochastic | CCI | 2 | 57 | 55 | 50 |
| 53 | B | Red | BASF .067" | 260 5.2 | Stochastic | CCI | 3 | 54 | 50 | 49 |
| 53 | C | Red | BASF .067" | 260 5.2 | Stochastic | CCI | 1 | 46 | 50 | 40 |
| 53 | C | Red | BASF .067" | 260 5.2 | Stochastic | CCI | 2 | 54 | 48 | 42 |
| 53 | C | Red | BASF .067" | 260 5.2 | Stochastic | CCI | 3 | 47 | 44 | 44 |
| 54 | A | Red | BASF .067" | 360 4.5 | Stochastic | CCI | 1 | 42 | 43 | 47 |
| 54 | A | Red | BASF .067" | 360 4.5 | Stochastic | CCI | 2 | 41 | 48 | 47 |
| 54 | A | Red | BASF .067" | 360 4.5 | Stochastic | CCI | 3 | 44 | 46 | 46 |
| 54 | B | Red | BASF .067" | 360 4.5 | Stochastic | CCI | 1 | 62 | 53 | 57 |
| 54 | B | Red | BASF .067" | 360 4.5 | Stochastic | CCI | 2 | 58 | 55 | 59 |
| 54 | B | Red | BASF .067" | 360 4.5 | Stochastic | CCI | 3 | 58 | 51 | 61 |
| 54 | C | Red | BASF .067" | 360 4.5 | Stochastic | CCI | 1 | 50 | 61 | 56 |
| 54 | C | Red | BASF .067" | 360 4.5 | Stochastic | CCI | 2 | 40 | 44 | 57 |
| 54 | C | Red | BASF .067" | 360 4.5 | Stochastic | CCI | 3 | 57 | 45 | 55 |

APPENDIX B

| | | | | | | | | Print Vibrancy - Trial 2 | | |
|---|---|---|---|---|---|---|---|---|---|---|
| | | | | | | | | | Sample | |
| Code | Substrate | Plate | Solvent | Viscosity | White primer | Treatment | Impression | 1 | 2 | 3 |
| 1 | A | Photo | 70/30 | 35 | No | Yes | Low | 56 | 47 | 53 |
| 1 | B | Photo | 70/30 | 35 | No | Yes | Low | 56 | 70 | 57 |
| 2 | A | Photo | 70/30 | 35 | Yes | Yes | Low | 50 | 47 | 48 |
| 2 | B | Photo | 70/30 | 35 | Yes | Yes | Low | 66 | 59 | 71 |
| 3 | A | Photo | 70/30 | 35 | No | No | Low | 51 | 51 | 42 |
| 3 | B | Photo | 70/30 | 35 | No | No | Low | 57 | 64 | 67 |
| 4 | A | Photo | 70/30 | 35 | Yes | No | Low | 53 | 53 | 45 |
| 4 | B | Photo | 70/30 | 35 | Yes | No | Low | 48 | 56 | 54 |
| 5 | A | Photo | 70/30 | 30 | No | Yes | Low | 42 | 43 | 43 |
| 5 | B | Photo | 70/30 | 30 | No | Yes | Low | 50 | 53 | 55 |
| 6 | A | Photo | 70/30 | 30 | Yes | Yes | Low | 43 | 41 | 47 |
| 6 | B | Photo | 70/30 | 30 | Yes | Yes | Low | 61 | 65 | 53 |
| 7 | A | Photo | 70/30 | 30 | No | No | Low | 45 | 42 | 43 |
| 7 | B | Photo | 70/30 | 30 | No | No | Low | 57 | 47 | 51 |
| 8 | A | Photo | 70/30 | 30 | Yes | No | Low | 44 | 44 | 44 |
| 8 | B | Photo | 70/30 | 30 | Yes | No | Low | 54 | 49 | 52 |
| 9 | A | Photo | 70/30 | 25 | No | Yes | Low | 46 | 48 | 44 |
| 10 | A | Photo | 70/30 | 25 | Yes | Yes | Low | 54 | 50 | 49 |
| 11 | A | Photo | 70/30 | 25 | No | No | Low | 46 | 44 | 47 |
| 11 | B | Photo | 70/30 | 25 | No | No | Low | 57 | 57 | 52 |
| 12 | B | Photo | 70/30 | 25 | Yes | No | Low | 55 | 59 | 56 |
| 13 | A | Photo | 70/30 | 20 | No | Yes | Low | 40 | 40 | 44 |
| 13 | B | Photo | 70/30 | 20 | No | Yes | Low | 51 | 58 | 55 |
| 14 | A | Photo | 70/30 | 20 | Yes | Yes | Low | 44 | 40 | 42 |
| 14 | B | Photo | 70/30 | 20 | Yes | Yes | Low | 58 | 58 | 54 |
| 15 | A | Photo | 70/30 | 20 | No | No | Low | 51 | 49 | 50 |
| 15 | B | Photo | 70/30 | 20 | No | No | Low | 64 | 53 | 55 |
| 16 | A | Photo | 70/30 | 20 | Yes | No | Low | 45 | 39 | 42 |
| 16 | B | Photo | 70/30 | 20 | Yes | No | Low | 53 | 55 | 58 |
| 17 | A | Rubber | 70/30 | 35 | No | Yes | Low | 48 | 53 | 52 |
| 17 | B | Rubber | 70/30 | 35 | No | Yes | Low | 50 | 56 | 60 |
| 18 | A | Rubber | 70/30 | 35 | Yes | Yes | Low | 51 | 61 | 58 |
| 18 | B | Rubber | 70/30 | 35 | Yes | Yes | Low | 54 | 60 | 66 |
| 19 | A | Rubber | 70/30 | 35 | No | No | Low | 50 | 50 | 48 |

-continued

| | | | | | | | | Sample | | |
|---|---|---|---|---|---|---|---|---|---|---|
| Code | Substrate | Plate | Solvent | Viscosity | White primer | Treatment | Impression | 1 | 2 | 3 |
| 19 | B | Rubber | 70/30 | 35 | No | No | Low | 62 | 52 | 63 |
| 20 | A | Rubber | 70/30 | 35 | Yes | No | Low | 46 | 52 | 52 |
| 20 | B | Rubber | 70/30 | 35 | Yes | No | Low | 62 | 63 | 56 |
| 21 | A | Rubber | 70/30 | 30 | No | Yes | Low | 41 | 45 | 38 |
| 21 | B | Rubber | 70/30 | 30 | No | Yes | Low | 54 | 80 | 53 |
| 22 | A | Rubber | 70/30 | 30 | Yes | Yes | Low | 46 | 51 | 39 |
| 22 | B | Rubber | 70/30 | 30 | Yes | Yes | Low | 58 | 55 | 62 |
| 23 | A | Rubber | 70/30 | 30 | No | No | Low | 41 | 40 | 37 |
| 23 | B | Rubber | 70/30 | 30 | No | No | Low | 58 | 50 | 54 |
| 24 | A | Rubber | 70/30 | 30 | Yes | No | Low | 46 | 36 | 39 |
| 24 | B | Rubber | 70/30 | 30 | Yes | No | Low | 58 | 53 | 59 |
| 25 | A | Rubber | 70/30 | 25 | No | Yes | Low | 43 | 44 | 45 |
| 26 | A | Rubber | 70/30 | 25 | Yes | Yes | Low | 49 | 52 | 48 |
| 27 | A | Rubber | 70/30 | 25 | No | No | Low | 44 | 46 | 38 |
| 27 | B | Rubber | 70/30 | 25 | No | No | Low | 52 | 60 | 55 |
| 28 | B | Rubber | 70/30 | 25 | Yes | No | Low | 67 | 65 | 68 |
| 29 | A | Rubber | 70/30 | 20 | No | Yes | Low | 43 | 40 | 40 |
| 29 | B | Rubber | 70/30 | 20 | No | Yes | Low | 52 | 54 | 48 |
| 30 | A | Rubber | 70/30 | 20 | Yes | Yes | Low | 40 | 43 | 38 |
| 30 | B | Rubber | 70/30 | 20 | Yes | Yes | Low | 39 | 61 | 57 |
| 31 | A | Rubber | 70/30 | 20 | No | No | Low | 40 | 45 | 47 |
| 31 | B | Rubber | 70/30 | 20 | No | No | Low | 59 | 51 | 55 |
| 32 | A | Rubber | 70/30 | 20 | Yes | No | Low | 42 | 41 | 38 |
| 32 | B | Rubber | 70/30 | 20 | Yes | No | Low | 56 | 59 | 55 |
| 33 | A | Texture | 70/30 | 35 | No | Yes | Low | 51 | 54 | 47 |
| 33 | B | Texture | 70/30 | 35 | No | Yes | Low | 62 | 68 | 58 |
| 34 | A | Texture | 70/30 | 35 | Yes | Yes | Low | 51 | 49 | 50 |
| 34 | B | Texture | 70/30 | 35 | Yes | Yes | Low | 66 | 55 | 71 |
| 35 | A | Texture | 70/30 | 35 | No | No | Low | 52 | 48 | 51 |
| 35 | B | Texture | 70/30 | 35 | No | No | Low | 65 | 54 | 67 |
| 36 | A | Texture | 70/30 | 35 | Yes | No | Low | 49 | 49 | 52 |
| 36 | B | Texture | 70/30 | 35 | Yes | No | Low | 59 | 67 | 63 |
| 37 | A | Texture | 70/30 | 30 | No | Yes | Low | 42 | 42 | 38 |
| 37 | B | Texture | 70/30 | 30 | No | Yes | Low | 53 | 48 | 50 |
| 38 | A | Texture | 70/30 | 30 | Yes | Yes | Low | 46 | 43 | 47 |
| 38 | B | Texture | 70/30 | 30 | Yes | Yes | Low | 50 | 52 | 55 |
| 39 | A | Texture | 70/30 | 30 | No | No | Low | 41 | 40 | 44 |
| 39 | B | Texture | 70/30 | 30 | No | No | Low | 46 | 57 | 47 |
| 40 | A | Texture | 70/30 | 30 | Yes | No | Low | 43 | 40 | 43 |
| 40 | B | Texture | 70/30 | 30 | Yes | No | Low | 57 | 56 | 53 |
| 41 | A | Texture | 70/30 | 25 | No | Yes | Low | 46 | 46 | 47 |
| 42 | A | Texture | 70/30 | 25 | Yes | Yes | Low | 52 | 48 | 48 |
| 43 | A | Texture | 70/30 | 25 | No | No | Low | 46 | 48 | 48 |
| 43 | B | Texture | 70/30 | 25 | No | No | Low | 56 | 55 | 59 |
| 44 | B | Texture | 70/30 | 25 | Yes | No | Low | 56 | 64 | 53 |
| 45 | A | Texture | 70/30 | 20 | No | Yes | Low | 39 | 42 | 38 |
| 46 | A | Texture | 70/30 | 20 | Yes | Yes | Low | 44 | 36 | 41 |
| 47 | A | Texture | 70/30 | 20 | No | No | Low | 46 | 45 | 50 |
| 48 | A | Texture | 70/30 | 20 | Yes | No | Low | 46 | 41 | 39 |
| 49 | A | Photo | 50/50 | 35 | No | Yes | Low | 56 | 55 | 55 |
| 49 | B | Photo | 50/50 | 35 | No | Yes | Low | 64 | 62 | 58 |
| 50 | A | Photo | 50/50 | 35 | Yes | Yes | Low | 52 | 54 | 58 |
| 50 | B | Photo | 50/50 | 35 | Yes | Yes | Low | 54 | 56 | 61 |
| 51 | A | Photo | 50/50 | 35 | No | No | Low | 51 | 53 | 58 |
| 51 | B | Photo | 50/50 | 35 | No | No | Low | 70 | 76 | 72 |
| 52 | A | Photo | 50/50 | 35 | Yes | No | Low | 47 | 51 | 55 |
| 52 | B | Photo | 50/50 | 35 | Yes | No | Low | 56 | 62 | 68 |
| 55 | A | Photo | 50/50 | 30 | No | No | Low | 60 | 62 | 58 |
| 55 | B | Photo | 50/50 | 30 | No | No | Low | 70 | 71 | 69 |
| 56 | A | Photo | 50/50 | 30 | Yes | No | Low | 62 | 61 | 59 |
| 56 | B | Photo | 50/50 | 30 | Yes | No | Low | 79 | 72 | 73 |
| 58 | A | Photo | 50/50 | 25 | No | No | Low | 57 | 56 | 58 |
| 58 | B | Photo | 50/50 | 25 | No | No | Low | 67 | 68 | 70 |
| 65 | A | Rubber | 50/50 | 35 | No | Yes | Low | 48 | 53 | 54 |
| 65 | B | Rubber | 50/50 | 35 | No | Yes | Low | 67 | 63 | 58 |
| 66 | A | Rubber | 50/50 | 35 | Yes | Yes | Low | 53 | 52 | 52 |
| 66 | B | Rubber | 50/50 | 35 | Yes | Yes | Low | 51 | 62 | 57 |
| 67 | A | Rubber | 50/50 | 35 | No | No | Low | 48 | 48 | 47 |
| 67 | B | Rubber | 50/50 | 35 | No | No | Low | 66 | 59 | 59 |
| 68 | B | Rubber | 50/50 | 35 | Yes | No | Low | 58 | 65 | 61 |
| 71 | A | Rubber | 50/50 | 30 | No | No | Low | 58 | 57 | 58 |
| 71 | B | Rubber | 50/50 | 30 | No | No | Low | 58 | 67 | 58 |
| 72 | A | Rubber | 50/50 | 30 | Yes | No | Low | 59 | 63 | 62 |
| 72 | B | Rubber | 50/50 | 30 | Yes | No | Low | 74 | 72 | 70 |

Print Vibrancy - Trial 2 (continued)

| Code | Substrate | Plate | Solvent | Viscosity | White primer | Treatment | Impression | Sample 1 | 2 | 3 |
|---|---|---|---|---|---|---|---|---|---|---|
| 75 | A | Rubber | 50/50 | 25 | No | No | Low | 59 | 61 | 58 |
| 75 | B | Rubber | 50/50 | 25 | No | No | Low | 68 | 63 | 64 |
| 81 | A | Texture | 50/50 | 35 | No | Yes | Low | 54 | 53 | 51 |
| 81 | B | Texture | 50/50 | 35 | No | Yes | Low | 73 | 64 | 54 |
| 82 | A | Texture | 50/50 | 35 | Yes | Yes | Low | 51 | 51 | 50 |
| 82 | B | Texture | 50/50 | 35 | Yes | Yes | Low | 59 | 64 | 63 |
| 83 | A | Texture | 50/50 | 35 | No | No | Low | 44 | 52 | 50 |
| 83 | B | Texture | 50/50 | 35 | No | No | Low | 71 | 72 | 55 |
| 84 | A | Texture | 50/50 | 35 | Yes | No | Low | 52 | 55 | 53 |
| 84 | B | Texture | 50/50 | 35 | Yes | No | Low | 66 | 66 | 62 |
| 87 | A | Texture | 50/50 | 30 | No | No | Low | 57 | 55 | 59 |
| 87 | B | Texture | 50/50 | 30 | No | No | Low | 67 | 71 | 70 |
| 88 | A | Texture | 50/50 | 30 | Yes | No | Low | 59 | 68 | 63 |
| 88 | B | Texture | 50/50 | 30 | Yes | No | Low | 71 | 74 | 68 |
| 91 | A | Texture | 50/50 | 25 | No | No | Low | 52 | 56 | 54 |
| 91 | B | Texture | 50/50 | 25 | No | No | Low | 59 | 58 | 59 |
| 100 | A | Photo | 50/50 | 35 | No | No | High | 61 | 54 | 63 |
| 101 | A | Rubber | 50/50 | 35 | No | No | High | 58 | 61 | 64 |
| 102 | A | Texture | 50/50 | 35 | No | No | High | 54 | 62 | 60 |
| 102 | B | Texture | 50/50 | 35 | No | No | High | 71 | 66 | 68 |

APPENDIX C

Print Vibrancy - Trial 3

| Basis Weight | Sheath Polymer | Laminate | Ink Density | Average | SD |
|---|---|---|---|---|---|
| 0.6 | PP | Y | 64 | | |
| 0.6 | PP | Y | 66 | | |
| 0.6 | PP | Y | 59 | | |
| 0.6 | PP | Y | 69 | 64.5 | 4.2 |
| 0.6 | PE | Y | 68 | | |
| 0.6 | PE | Y | 74 | | |
| 0.6 | PE | Y | 79 | | |
| 0.6 | PE | Y | 69 | 72.5 | 5.1 |
| 1.0 | PP | Y | 57 | | |
| 1.0 | PP | Y | 53 | | |
| 1.0 | PP | Y | 55 | | |
| 1.0 | PP | Y | 57 | 55.5 | 1.9 |
| 1.0 | PE | Y | 68 | | |
| 1.0 | PE | Y | 66 | | |
| 1.0 | PE | Y | 73 | | |
| 1.0 | PE | Y | 69 | 69.0 | 2.9 |
| 0.6 | PP | N | 55 | | |
| 0.6 | PP | N | 63 | | |
| 0.6 | PP | N | 44 | | |
| 0.6 | PP | N | 55 | 54.3 | 7.8 |
| 0.6 | PE | N | 69 | | |
| 0.6 | PE | N | 61 | | |
| 0.6 | PE | N | 66 | | |
| 0.6 | PE | N | 53 | 62.8 | 7.4 |
| 1.0 | PP | N | 62 | | |
| 1.0 | PP | N | 53 | | |
| 1.0 | PP | N | 56 | | |
| 1.0 | PP | N | 59 | 57.5 | 8.9 |
| 1.0 | PE | N | 69 | | |
| 1.0 | PE | N | 63 | | |
| 1.0 | PE | N | 64 | | |
| 1.0 | PE | N | 63 | 64.8 | 2.9 |

APPENDIX D

Print Vibrancy - Trial 4

| | Color Density | | | |
|---|---|---|---|---|
| | Magenta | Cyan | Black | Yellow |
| Substrate A | | | | |
| 1 | 0.84 | 0.69 | 0.83 | 0.61 |
| 2 | 0.83 | 0.75 | 0.82 | 0.52 |
| 3 | 0.68 | 0.73 | 0.85 | 0.65 |
| 4 | 0.79 | 0.82 | 0.83 | 0.62 |
| 5 | 0.87 | 0.83 | 0.80 | 0.60 |
| Avg | 0.80 | 0.76 | 0.83 | 0.60 |
| Std Dev | 0.07 | 0.06 | 0.02 | 0.05 |
| Substrate B | | | | |
| 1 | 0.83 | 0.63 | 0.68 | 0.54 |
| 2 | 0.66 | 0.62 | 0.63 | 0.65 |
| 3 | 0.71 | 0.68 | 0.65 | 0.59 |
| 4 | 0.66 | 0.69 | 0.58 | 0.52 |
| 5 | 0.72 | 0.59 | 0.62 | 0.52 |
| Avg | 0.72 | 0.64 | 0.63 | 0.56 |
| Std Dev | 0.07 | 0.04 | 0.04 | 0.06 |
| Substrate C | | | | |
| 1 | 0.65 | 0.55 | 0.67 | 0.48 |
| 2 | 0.57 | 0.57 | 0.62 | 0.49 |
| 3 | 0.6 | 0.58 | 0.6 | 0.5 |
| 4 | 0.62 | 0.57 | 0.6 | 0.48 |
| 5 | 0.65 | 0.54 | 0.65 | 0.49 |
| Avg | 0.62 | 0.56 | 0.63 | 0.49 |
| Std Dev | 0.03 | 0.02 | 0.03 | 0.01 |

APPENDIX E

| Print Vibrancy - Trial 5 | | | | |
| --- | --- | --- | --- | --- |
| | Color Density | | | |
| | Magenta | Cyan | Black | Yellow |
| Sample A | | | | |
| 1 | 0.46 | 0.20 | 0.44 | 0.34 |
| 2 | 0.46 | 0.17 | 0.41 | 0.35 |
| 3 | 0.42 | 0.17 | 0.44 | 0.33 |
| 4 | 0.44 | 0.25 | 0.41 | 0.38 |
| 5 | 0.37 | 0.31 | 0.40 | 0.32 |
| Avg | 0.43 | 0.22 | 0.42 | 0.34 |
| Std Dev | 0.04 | 0.06 | 0.02 | 0.02 |
| Sample B | | | | |
| 1 | 0.55 | 0.67 | 0.66 | 0.43 |
| 2 | 0.56 | 0.65 | 0.61 | 0.45 |
| 3 | 0.49 | 0.62 | 0.68 | 0.42 |
| 4 | 0.57 | 0.67 | 0.70 | 0.47 |
| 5 | 0.59 | 0.63 | 0.67 | 0.38 |
| Avg | 0.55 | 0.65 | 0.66 | 0.43 |
| Std Dev | 0.04 | 0.02 | 0.03 | 0.03 |

What is claimed is:

1. A process for making a non-woven substrate having a vibrant graphic applied thereto, said process comprising:
feeding to a printing apparatus a non-woven substrate comprising a fibrous non-woven web composed at least in part of polyolefin fibers;
supplying the printing apparatus with an ink composition having a viscosity in the range of about 28 seconds to about 35 seconds as determined using a Zahn #2 cup and comprising at least one solvent having an evaporation rate relative to n-butyl acetate of less than 0.8;
operating the printing apparatus to apply the ink composition to the fibrous non-woven web while the fibrous non-woven web is in a dry condition to form a graphic thereon having a thickness of less than or equal to about 5 microns; and
allowing the ink composition to dry on the fibrous non-woven web.

2. The process set forth in claim 1 wherein the step of feeding a non-woven substrate to the printing apparatus comprises feeding to said printing apparatus a non-woven substrate comprised at least in part of a fibrous non-woven web composed at least in part of polyethylene fibers.

3. The process set forth in claim 1 wherein at least a portion of the graphic has a dominant primary color of magenta having a color density of at least about 0.5 as determined by a Color Density Test.

4. The process set forth in claim 3 wherein at least a portion of the graphic has a dominant primary color of magenta having a color density of at least about 0.6 as determined by a Color Density Test.

5. The process set forth in claim 4 wherein at least a portion of the graphic has a dominant primary color of magenta having a color density of at least about 0.7 as determined by a Color Density Test.

6. The process set forth in claim 5 wherein at least a portion of the graphic has a dominant primary color of magenta having a color density of at least about 0.8 as determined by a Color Density Test.

7. The process set forth in claim 1 wherein at least a portion of the graphic has a dominant primary color of black having a color density of at least about 0.5 as determined by a Color Density Test.

8. The process set forth in claim 7 wherein at least a portion of the graphic has a dominant primary color of black having a color density of at least about 0.6 as determined by a Color Density Test.

9. The process set forth in claim 8 wherein at least a portion of the graphic has a dominant primary color of black having a color density of at least about 0.7 as determined by a Color Density Test.

10. The process set forth in claim 9 wherein at least a portion of the graphic has a dominant primary color of black having a color density of at least about 0.8 as determined by a Color Density Test.

11. The process set forth in claim 1 wherein at least a portion of the graphic has a dominant primary color of cyan having a color density of at least about 0.5 as determined by a Color Density Test.

12. The process set forth in claim 11 wherein at least a portion of the graphic has a dominant primary color of cyan having a color density of at least about 0.6 as determined by a Color Density Test.

13. The process set forth in claim 12 wherein at least a portion of the graphic has a dominant primary color of cyan having a color density of at least about 0.7 as determined by a Color Density Test.

14. The process set forth in claim 13 wherein at least a portion of the graphic has a dominant primary color of cyan having a color density of at least about 0.75 as determined by a Color Density Test.

15. The process set forth in claim 1 wherein at least a portion of the graphic has a dominant primary color of yellow having a color density of at least about 0.5 as determined by a Color Density Test.

16. The process set forth in claim 15 wherein at least a portion of the graphic has a dominant primary color of yellow having a color density of at least about 0.55 as determined by a Color Density Test.

17. The process set forth in claim 16 wherein at least a portion of the graphic has a dominant primary color of yellow having a color density of at least about 0.6 as determined by a Color Density Test.

18. The process set forth in claim 1 wherein the printing apparatus is a flexographic printing apparatus.

19. The process set forth in claim 18 wherein the step of operating the printing apparatus comprises operating the flexographic printing apparatus at a print plate set point relative to an impression cylinder of the apparatus in the range of about 0.115 to about 0.135 inches.

20. The process set forth in claim 1 wherein the step of supplying an ink composition comprises supplying an ink composition comprising at least one solvent having an evaporation rate relative to n-butyl acetate of less than about 0.5.

21. The process set forth in claim 20 wherein the step of supplying an ink composition comprises supplying an ink composition comprising at least one solvent having an evaporation rate relative to n-butyl acetate of less than about 0.25.

22. The process set forth in claim 21 wherein the at least one solvent comprises propylene glycol n-propyl ether (PnP).

23. The process set forth in claim 1 wherein the ink composition has a viscosity in the range of about 28 to about 32 seconds using a Zahn #2 cup.

24. The process set forth in claim 18 wherein the step of operating the printing apparatus comprises operating the flexographic printing apparatus in a block type printing process to apply the ink composition to the fibrous non-woven web.

* * * * *